(12) United States Patent
Nagai et al.

(10) Patent No.: US 7,647,290 B2
(45) Date of Patent: Jan. 12, 2010

(54) METHOD FOR PERFORMING BIOINFORMATICS ANALYSIS PROGRAM AND BIOINFORMATICS ANALYSIS PLATFORM

(75) Inventors: Tateo Nagai, Tokyo (JP); Daniel Reda, Alameda, CA (US); Takahiko Kasuga, Tokyo (JP); Yasuyuki Nozaki, Tokyo (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 464 days.

(21) Appl. No.: 11/593,173

(22) Filed: Nov. 6, 2006

(65) Prior Publication Data
US 2008/0125975 A1 May 29, 2008

(51) Int. Cl.
*G06F 15/00* (2006.01)
(52) U.S. Cl. .................... 706/62; 706/11; 706/45; 702/19; 702/22; 703/11
(58) Field of Classification Search .............. 706/11, 706/45–48, 50, 60, 62; 702/19–32; 703/11
See application file for complete search history.

(56) References Cited

U.S. PATENT DOCUMENTS 6,125,383 A * 9/2000 Glynias et al. .............. 709/202
7,231,390 B2 * 6/2007 Blair et al. ..................... 707/6
2001/0053957 A1 * 12/2001 Blair et al. .................... 702/19
2004/0068514 A1 * 4/2004 Chundi et al. ............... 707/102
2008/0125975 A1 * 5/2008 Nagai et al. .................. 702/19
2009/0055147 A1 * 2/2009 Miyake et al. ............... 703/11

FOREIGN PATENT DOCUMENTS

JP 2005-228155 2/2004

OTHER PUBLICATIONS

Otsuka et al., Machine translation of Japanese Patent Application JP 2005-228155, pp. 1-32.*

* cited by examiner

*Primary Examiner*—David R Vincent
*Assistant Examiner*—Omar F Fernandez Rivas
(74) *Attorney, Agent, or Firm*—Stites & Harbison PLLC; Juan Carlos A. Marquez, Esq.

(57) ABSTRACT

A system in which researchers can freely and effectively use worldwide bioinformatics analysis programs available on the Internet is provided. When a bioinformatics analysis program available on the Internet is used by a user computer, a broker program is used. The broker program has a function of absorbing differences in input/output format between analysis programs, and each analysis program is provided with the broker program. A broker program-providing server stores various broker programs provided by users and makes them available to the public. When the user uses bioinformatics analysis programs available on the Internet, the user can use broker programs that are made available by the broker program-providing server and that are created by other users.

8 Claims, 22 Drawing Sheets

FIG. 3

```
Output of Analysis A

Score    E
Sequences producing significant alignments:               (Bits)   Value 301 ⎰ gi|12345678|emb|AL2198129.3|  Human DNA sequence from clone    38.2   3.7
    ⎱ gi|13456789|gb|AC3242232.6|   Homo sapiens BAC clone           38.2   3.7
      gi|19876543|gb|AC9232392.3|   Homo sapiens chromosome 3 clone  38.2   3.7

ALIGNMENTS
> gi|12345678|emb|AL2198129.3|  Human DNA sequence from clone
Length=159845

Score = 38.2 bits (19),  Expect = 3.7
302 ⎰ Strand=Plus/Plus

Query   8      TCTGTCATCATCATTATATGCC   26
               |||||||||||||||||||||
Sbjct   75288  TCTGTCATCATCATTATATGCC   75306

//

> gi|13456789|gb|AC3242232.6 |  Homo sapiens BAC clone
Length=100743

Score = 35.0 bits (19),  Expect = 3.7
303 ⎰ Strand=Plus/Minus

Query   2      CTACAGTCTGTCATCATTATATG   24
               |||||  ||||||||||||||||
Sbjct   3677   CTACACTCTGTCATCATTATATG   3655

//

> gi|19876543|gb|AC9232392.3|  Homo sapiens chromosome 3 clone
Length=156180

Score = 38.2 bits (19),  Expect = 3.7
304 ⎰ Strand=Plus/Plus

Query   10     TGTCATCATTATATGCCTAGCAT   32
               ||||||||||||||||| ||||||
Sbjct   67206  TGTCATCATTATATGCTTAGCAT   67228

```
<imputParamInfo>
    <param>
            <name>Sequence Name:</name>
            <inputform>textbox</inputform>
            <options></options>
            <defaultVal></defaultVal>
            <dataType>SEQ_NAME</dataType>
            <sendName>seqname</sendName>
    </param>
    <param>
            <name>Sequence Type:</name>
            <inputform>pulldown</inputform>
            <options>
                    <item value= "dna" >DNA</item>
                    <item value= "protein" >Protein</item>
            </options>
            <defaultVal>DNA</defaultVal>
            <dataType>SEQ_TYPE</dataType>
            <sendName>type</sendName>
    </param>
    <param>
            <name>Sequence:</name>
            <inputform>textbox</inputform>
            <options>
                    <item value= "hum_dna" >Human DNA</item>
                    <item value= "hum_rna" >Human RNA</item>
                    <item value= "hum" >Human</item>
                    <item value= "protein" >Protein</item>
                    <item value= "rat" >Rat Genome</item>
            </options>
            <defaultVal>Human DNA</defaultVal>
            <dataType>SEQ</dataType>
            <sendName>sequence</sendName>
    </param>
    <param>
            <name>Matrix:</name>
            <inputform>pulldown</inputform>
            <options>
                    <item value= "Blossom 2" >Blossom 2</item>
                    <item value= "Blossom 24" >Blossom 24</item>
            </options>
            <defaultVal>Blossom 2</defaultVal>
            <dataType>MATRIX</dataType>
            <sendName>matrix</sendName>
    </param>
    <param>
            <name>Threshold:</name>
            <inputform>textbox</inputform>
            <options></options>
            <defaultVal>32</defaultVal>
            <dataType>INTEGER</dataType>
            <sendName>threshold</sendName>
    </param>
    <param>
            <name>Priority:</name>
            <inputform>radio</inputform>
            <options>
                    <item value= "quality" >Quality</item>
                    <item value= "speed" >Speed</item>
            </options>
            <defaultVal>Quality</defaultVal>
            <dataType>STRING</dataType>
            <sendName>priority</sendName>
    </param>
</imputParamInfo>
```

- 401: Sequence Name param
- 402: Sequence Type param
- 403: Sequence param
- 404: Matrix param
- 405: Threshold param
- 406: Priority param

FIG. 5

```
<extractRule>
    <block>
        <start matchLine="this">Sequences producing significant alignments:</start>
        <end matchLine="before">ALIGNMENTS</end>

<table>
            <TABLE_TITLE></TABLE_TITLE>
            <COLUMN>
                <NAME>GI</NAME>
                <DATA>¥n{0}¥s+.+</DATA>
            </COLUMN>
            <COLUMN>
                <NAME>sequence name</NAME>
                <DATA>gi.+¥s+{1}¥s[0-9]+¥.¥[0-9]¥s+[0-9]+¥.¥[0-9]¥n</DATA>
            </COLUMN>
            <COLUMN>
                <NAME>Score</NAME>
                <DATA>gi.+¥s+.+¥s+{2}¥s+[0-9]+¥.¥[0-9]¥n</DATA>
            </COLUMN>
            <COLUMN>
                <NAME>E value</NAME>
                <DATA>gi.+¥s+.+¥s+{3}¥n</DATA>
            </COLUMN>
        </table>
    </block>

<block>
        <start matchLine="this"></start>
        <end matchLine="before">//</end>

<alignment>
            <SCORE>Score={0}bits</SCORE>
            <EXPECT>Expect={1}¥n</EXPECT>
            <SEQ1>Query¥s+[0-9]+¥s+{2}¥s</SEQ1>
            <SEQ2>Sbjct¥s+[0-9]+¥s+{3}¥s</SEQ2>
            <SEQ1_START>Strand=.+¥nQuery¥s+{4}¥s</SEQ1_START>
            <SEQ2_START>Strand=.+¥nQuery.+¥n.*¥nSbjct¥s+{5}¥s</SEQ2_START>
            <SEQ1_STRAND>Strand={6}/</SEQ1_STRAND>
            <SEQ2_STRAND>Strand=(Plus|Minus)/{7}¥n</SEQ2_STRAND>
            <SBJCT_NAME>>{8}¥n</SBJCT_NAME>
            <MIDLINE>Query.+¥n¥s+{9}¥n</MIDLINE>
        </alignment>
    </block>
</extractRule>
```

501 — first block
502 — second block

FIG. 6

```
<metadata>
    <table>
        <row>
            <cell colName="GI">gi|12345678|emb|AL2198129.3|</cell>
            <cell colName="sequence name">Human DNA sequence from clone</cell>
            <cell colName="Score">38.2</cell>
            <cell colName="E value">3.7</cell>
        </row>
        <row>
            <cell colName="GI">gi|13456789|gb|AC3242232.6|</cell>
            <cell colName="sequence name">Homo sapiens BAC clone</cell>
            <cell colName="Score">36.7</cell>
            <cell colName="E value">3.7</cell>
        </row>
        <row>
            <cell colName="GI">gi|19876543|gb|AC9232392.3|</cell>
            <cell colName="sequence name">Homo sapiens chromosome 3 clone</cell>
            <cell colName="Score">35.0</cell>
            <cell colName="E value">3.7</cell>
        </row>
    </table>
    <alignment>
        <SCORE>38.2</SCORE>
        <EXPECT>3.7</EXPECT>
        <SEQ1>TCTGTCATCATTATATGCC</SEQ1>
        <SEQ2>TCTGTCATCATTATATGCC</SEQ2>
        <SEQ1_START>8</SEQ1_START>
        <SEQ2_START>75288</SEQ2_START>
        <SEQ1_STRAND>Plus</SEQ1_STRAND>
        <SEQ2_STRAND>Plus</SEQ2_STRAND>
        <SBJCT_NAME>gi|12345678|emb|AL2198129.3| Human DNA sequence from clone</SBJCT_NAME>
        <MIDLINE>|||||||||||||||||||</MIDLINE>
    </alignment>
    <alignment>
        <SCORE>38.2</SCORE>
        <EXPECT>3.7</EXPECT>
        <SEQ1>CTACAGTCTGTCATCATTATATG</SEQ1>
        <SEQ2>CTACACTCTGTCATCATTATATG</SEQ2>
        <SEQ1_START>2</SEQ1_START>
        <SEQ2_START>3677</SEQ2_START>
        <SEQ1_STRAND>Plus</SEQ1_STRAND>
        <SEQ2_STRAND>Minus</SEQ2_STRAND>
        <SBJCT_NAME>gi|13456789|gb|AC3242232.6 | Homo sapiens BAC clone </SBJCT_NAME>
        <MIDLINE>|||||  |||||||||||||||||</MIDLINE>
    </alignment>
    <alignment>
        <SCORE>38.2</SCORE>
        <EXPECT>3.7</EXPECT>
        <SEQ1>TCTGTCATCATTATATGCC</SEQ1>
        <SEQ2>TCTGTCATCATTATATGCC</SEQ2>
        <SEQ1_START>10</SEQ1_START>
        <SEQ2_START>67206</SEQ2_START>
        <SEQ1_STRAND>Plus</SEQ1_STRAND>
        <SEQ2_STRAND>Plus</SEQ2_STRAND>
        <SBJCT_NAME>gi|19876543|gb|AC9232392.3| Homo sapiens chromosome 3 clone </SBJCT_NAME>
        <MIDLINE>||||||||||||||| ||||||</MIDLINE>
    </alignment>
</metadata>
```

FIG. 8

ANALYSIS PLATFORM

Tool Box | Preferences

New Tools and for Download
New Tool 1 – Description....
New Tool 2 – Description....
New Tool31 – Description....

Recently Used Tools
NCBI BLAST
ClustalW Alignment
Primer3 Search
Analysis Tool A

Help

---

Page | Insert | Outlining

New Page | Page 7 | Page 6 | Page 5 | Page 4 | Page 3

PARAMETER INPUT FORM

Sequence Name: 
Sequence Type: DNA
Sequence: 
Database: Human DNA
Matrix: Blossom 2
Threshold: 32

TABLE VIEWER

| GI | sequence name | Score | E-Value |
|---|---|---|---|
| gi\|12345678\|emb\|AL2198129.3\| | Human DNA sequence from clone | 38.2 | 3.7 |
| gi\|13456789\|gb\|AC3242232.6\| | Homo sapiens BAC clone | 36.7 | 3.7 |
| gi\|19876543\|gb\|AC9232392.3\| | Homo sapiens chromosome 3 clone | 35.0 | 3.7 |

ALIGNMENT VIEWER

```
gi|12345678|emb|AL2198129.3| Human DNA sequence from clone
Length=159845

Score = 38.2 bits (19),  Expect = 3.7
 Strand=Plus/Plus

Query  8      TCTGTCATCATTATATGCC  26
              |||||||||||||||||||
Sbjct  75288  TCTGTCATCATTATATGCC  75306
```

INPUT FORM INTERPRETATION RESULT

| | NAMES | INPUT FORMS | ALTERNATIVES | INITIAL VALUES | DATA TYPES |
|---|---|---|---|---|---|
| 1 | Sequence Name: | TEXT BOX | | | SEQ_NAME |
| 2 | Sequence Type: | PULLDOWN | DNA, Protein | DNA | SEQ_TYPE |
| 3 | Sequence: | | | | SEQ |
| 4 | Database: | | Human DNA, Human RNA, Human Protein Rat Genome, ... | Human DNA | |
| 5 | Matrix: | | Blossom 2, Blossom 24 | Blossom 2 | |
| 6 | Threshold: | | | 32 | |
| 7 | Priority: | RADIO BUTTON | Quality, Speed | Quality | |

[ CREATION OF INPUT PARAMETER INFORMATION ]

FIG. 14

```
TEST EXECUTION ON BROKER PROGRAM CREATION GRAPHIC IMAGE        □ ⊠

Output of Analysis A

Score      E
Sequences producing significant alignments:            (Bits)    Value gi|12345678|emb|AL2198129.3|  Human DNA sequence from clone    38.2   3.7
gi|13456789|gb|AC3242232.6|   Homo sapiens BAC clone           38.2   3.7
gi|19876543|gb|AC9232392.3|   Homo sapiens chromosome 3 clone  38.2   3.7

ALIGNMENTS
> gi|12345678|emb|AL2198129.3|  Human DNA sequence from clone
Length=159845

Score = 38.2 bits (19),  Expect = 3.7
 Strand=Plus/Plus

Query  8      TCTGTCATCATTATATGCC  26
              |||||||||||||||||||
Sbjct  75288  TCTGTCATCATTATATGCC  75306

//

> gi|13456789|gb|AC3242232.6 |  Homo sapiens BAC clone
Length=100743

Score = 36.7 bits (19),  Expect = 3.7
 Strand=Plus/Minus

Query  2      CTACAGTCTGTCATCATTATATG  24
              |||||  ||||||||||||||||
Sbjct  3677   CTACACTCTGTCATCATTATATG  3655

//

> gi|19876543|gb|AC9232392.3|  Homo sapiens chromosome 3 clone
```

METHOD FOR PERFORMING BIOINFORMATICS ANALYSIS PROGRAM AND BIOINFORMATICS ANALYSIS PLATFORM

BACKGROUND OF THE INVENTION

1. Field of the Invention

The present invention relates to computer analysis technology in the field of research in life science. Particularly, it relates to technology for executing a bioinformatics analysis program available on the Internet.

2. Background Art

The development of the field of research in life science has been remarkable over the past dozen years or so. Especially, rapid growth has been achieved in bioinformatics due to improvements in the performance and ease of computers. Life science is a field that requires further computing power, along with space physics, and a similar development is continuously expected.

Currently, various bioinformatics analysis programs or tools are available on the Internet. These analysis programs are added and updated daily by researchers all over the world. However, the current situation is that general researchers cannot keep up with the pace of an increase in the number of these analysis programs and the pace of progress thereof. There are two reasons for such problems: (1) many of the up-to-date bioinformatics analysis programs and tools are made publicly available as the command line programs of UNIX (trademark of X/Open Company Ltd.) or Windows OS (trademark of Microsoft Corporation). Thus, these tools are not necessarily easily used by general researchers who are not familiar with these programs; and (2) in order to obtain an up-to-date analysis program, the user needs to make efforts to obtain information by him/herself. Researchers having a great deal of work do not have time for continuously and completely watching worldwide up-to-date information available on the Internet.

Thus, researchers have no choice but to use general-purpose analysis software programs having many functions. However, general-purpose analysis software programs generally lack flexibility, and they cannot deal with ever-increasing and ever-progressing analysis methods. Thus, it is impossible to use up-to-date analysis methods, and in the first place, it is practically impossible to support all the various fields of research.

Furthermore, since different files are outputted for individual analysis programs when analysis results are stored, it is difficult to save data or search for the results.

Patent Document 1: JP Patent Publication (Kokai) No. 2005-228155 A

SUMMARY OF THE INVENTION

As described above, currently, the number of bioinformatics analysis programs is continuously increasing at a remarkable pace, and they are scattered on the Internet. However, researchers are individually finding analysis programs necessary for their research for use. Thus, information relating to analysis programs used by other researchers cannot be shared.

It will be convenient if one of the experts in each field of research downloads an analysis program in the relevant field in a terminal and such analysis program is made available so that other researchers can use the program.

An object of the present invention is to provide a system in which researchers can freely and effectively use worldwide bioinformatics analysis programs available on the Internet.

In accordance with the present invention, when a bioinformatics analysis program available on the Internet is used by a user computer, a broker program is used. The broker program has a function of absorbing differences in input/output format between analysis programs, and each analysis program is provided with the broker program.

The broker program is composed of "input parameter information," "output-data reading information," and an "analysis program reference destination." The "input parameter information" is extracted from the input form of the analysis program. The "output-data reading information" represents conversion rules for converting analysis results by the analysis program into metadata. The metadata refers to data obtained by converting the analysis results by the analysis program into a format that can be interpreted by an analysis platform. The "analysis program reference destination" refers to a location where the analysis program actually exists, and it is the URL of an analysis server or a file path in a PC, for example.

A broker program-providing server stores various broker programs provided by users and makes such broker programs available to the public. When users use bioinformatics analysis programs available on the Internet, they can use broker programs that are made available by the broker program-providing server and that are created by other users.

When users create broker programs, the broker programs can be uploaded to the broker program-providing server, so that other users can use the broker programs.

Users can store analysis programs and broker programs obtained through the Internet in their computers; that is, in their analysis platforms.

According to the present invention, researchers can freely and effectively use worldwide bioinformatics analysis programs available on the Internet.

BRIEF DESCRIPTION OF THE DRAWINGS

FIG. 3 shows an example of a graphic image displaying analysis results by the bioinformatics analysis program available on the Internet.

FIG. 4 shows an example of input parameter information of which a broker program is composed.

FIG. 5 shows an example of output-data reading information of which the broker program is composed.

FIG. 6 shows an example of metadata.

FIG. 8 shows an example of an analysis platform graphic image displayed on a display unit of the analysis platform according to the present invention.

FIG. 12 shows an example of a graphic image displaying the results of extraction of input fields from the input form of the analysis program, displayed on the display unit of the analysis platform according to the present invention.

FIG. 14 shows an example of a graphic image displaying the analysis results obtained through the analysis of the test data by the analysis program, displayed on the display unit of the analysis platform according to the present invention.

DESCRIPTION OF PREFERRED EMBODIMENTS OF THE INVENTION

Figure 1:
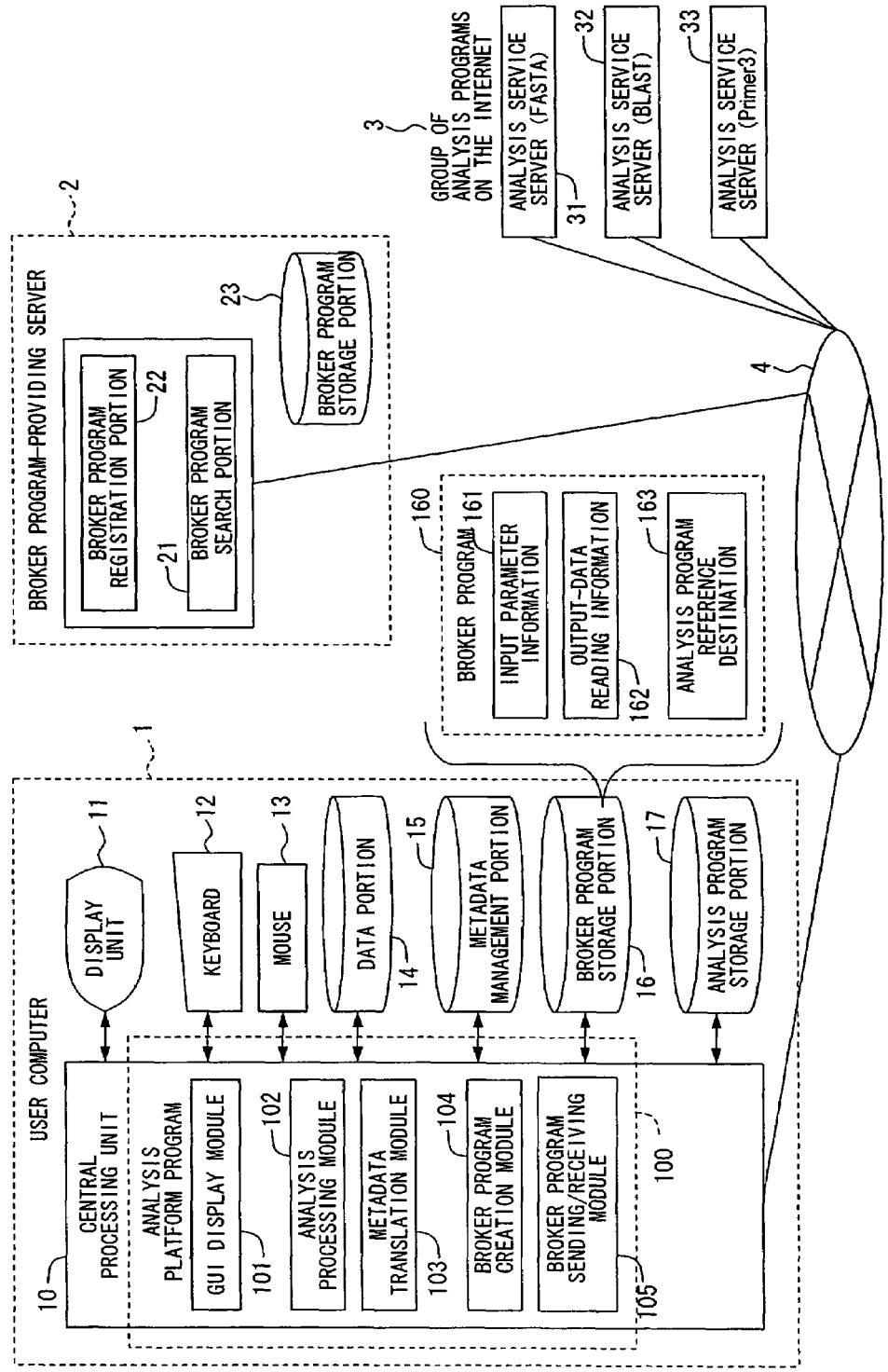
FIG. 1 shows a constitutional example of a bioinformatics analysis system according to the present invention.

FIG. 1 shows an example of a bioinformatics analysis system according to the present invention. The analysis system in the present example includes a user computer 1 used by a user. The user computer 1 is connected to a broker program-providing server 2 via the Internet 4 to which a group of bioinformatics analysis programs 3 is connected. Such group of analysis programs 3 are scattered on the Internet as analysis services provided by analysis service servers 31, 32, 33 and the like. FASTA, BLAST, Primer 3, and the like shown below are known for such group of analysis programs 3, for example.

FASTA (http://fasta.bioch.virginia.edu/fasta_www2/fasta_www.cgi?rm=select&pgm=fa)

BLAST (http://www.ncbi.nlm.nih.gov/BLAST/)

Primer 3 (http://frodo.wi.mit.edu/cgi-bin/primer3/primer3_www.cgi)

According to the present invention, various bioinformatics analysis programs 31 to 33, and the like available on the Internet 4 are accessed by the user computer 1 for use. According to the present invention, differences in input/output format between analysis programs are absorbed by a broker program 160. The broker program 160 is data in text file format, and it includes: input parameter information 161 for converting the input format of the analysis program into a format that can be interpreted by an analysis platform program 100; output-data reading information 162 for converting the output format of the analysis program into a format that can be interpreted by the analysis platform program 100; and an analysis program reference destination 163 for referring to the location where the analysis program actually exists (URL or a path in a PC).

The input parameter information is extracted from the input form of the analysis program. Namely, the input parameter information is information obtained by analyzing the input parameters of the analysis program and defining them in an XML format data. FIG. 4 shows an example of the input parameter information 161.

The output-data reading information 162 represents conversion rules for converting analysis results by the analysis program into metadata. Metadata refers to data obtained by converting the analysis results by the analysis program into a format that can be interpreted by the user computer; that is, the analysis platform program 100 in the present example. FIG. 6 shows an example of the metadata.

The analysis results by the bioinformatics analysis program generally have block structures. The output-data reading information 162 defines the corresponding relationship between blocks contained in the analysis results by the analysis program and metadata. Test data is analyzed by the analysis program, and as a result, the output-data reading information 162 is obtained. The analysis program reference destination 163 is the URL of an analysis server or a file path in a PC, for example.

A method for creating broker programs for the analysis platform of the present invention will be hereafter described with reference to the drawings. Note that instrument, a method, and the like used in the embodiment of the present invention are examples, and thus it goes without saying that the present invention is not limited thereto.

The user computer 1 includes a central processing unit 10, a display unit 11, a keyboard 12, a mouse 13, a data portion 14, a metadata management portion 15, a broker program storage portion 16, and an analysis program storage portion 17.

The display unit 11 displays an input form graphic image, an analysis result output graphic image, a broker program creation graphic image, or the like. The keyboard 12 and the mouse 13 are used by the user to perform operations, such as inputting or selecting data on the graphic image displayed on the display unit 11. The data portion 14 stores biopolymer data used in the analysis program. The metadata management portion 15 stores metadata. The broker program storage portion 16 stores broker programs. The analysis program storage portion 17 stores analysis programs that are executed in a local environment.

The central processing unit 10 executes the analysis platform program 100, so as to perform processes for creating instructions for analysis processing, creating a broker program, and displaying analysis results. The analysis platform program 100 includes a GUI display module 101, an analysis processing module 102, a metadata translation module 103, a broker program creation module 104, and a broker program sending/receiving module 105.

The GUI display module 101 displays various graphic images on the display unit 11. The analysis processing module 102 executes the analysis program by using the "input parameter information" of the broker program. The metadata translation module 103 changes the analysis results outputted by the analysis program into a metadata format by using the output-data reading information 162 of the broker program 160. The thus created metadata is stored in the metadata management portion 15. The broker program creation module 104 creates broker programs. The broker program sending/receiving module 105 uploads created broker programs to the broker program-providing server 2, and it downloads broker programs stored in the broker program-providing server 2. The broker program 160 created by the broker program creation module 104 and the broker program 160 downloaded by the broker program sending/receiving module 105 are stored in the broker program storage portion 16.

As described above, the broker program 160 includes the input parameter information 161, the output-data reading information 162, and the analysis program reference destination 163. The broker program-providing server 2 has a broker program registration portion 21, a broker program search portion 22, and a broker program storage portion 23.

The broker program storage portion 23 stores broker programs sent by user computers. Since the broker program stored in the broker program storage portion 23 has the same structure as that of the broker program 160, the structure thereof is not shown. The broker program registration portion 21 resisters the broker program sent by the user computer, and stores it in the broker program storage portion 23. The broker program search portion 22 searches the broker program storage portion 23 for a broker program.

In the bioinformatics analysis platform 1 in this example, there are two modes for executing the analysis program: one mode involving a case in which the analysis program stored in the analysis program storage portion 17 is executed; and the other mode involving a case in which the analysis program in the analysis program group 3 provided by the analysis service server 31, 32, 33 or the like on the Internet is executed. In the following explanation, the case in which the analysis program in the analysis program group on the Internet is executed by the user computer 1 will be described. The same processing is performed in the case in which the analysis program stored in the analysis program storage portion 17 of the user computer 1 is executed.

In the following description, the "analysis program" refers to a bioinformatics analysis program available on the Internet. While a user can access the analysis program, the analysis program is actually executed by the analysis service server that provides the analysis program. The user can obtain the analysis results by the analysis program.

Figure 2:
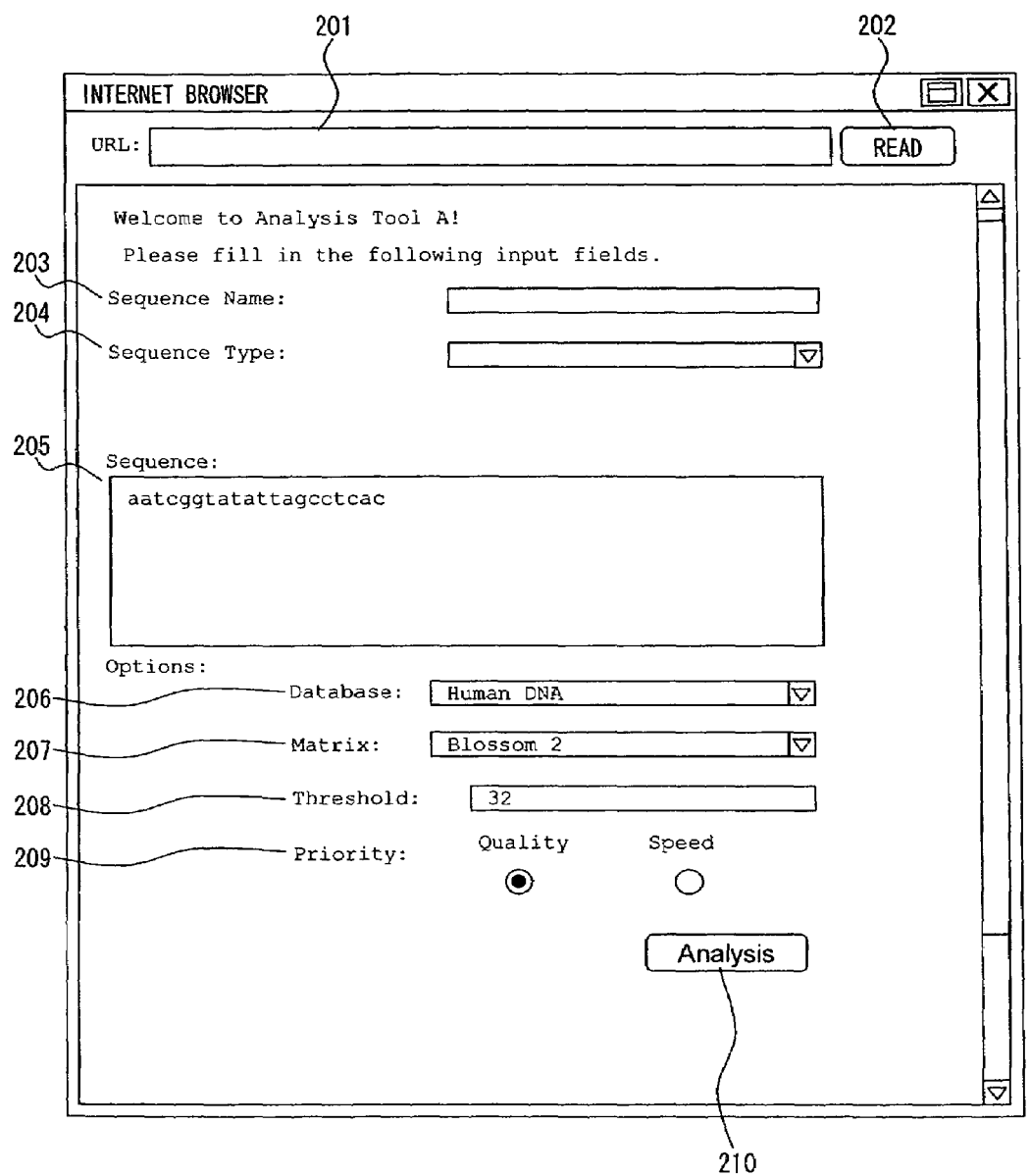
FIG. 2 shows an example of a parameter input graphic image of the bioinformatics analysis program available on the Internet.

FIG. 2 shows an example of the parameter input graphic image of the analysis program displayed on the display unit 11 of the user computer, when an actual analysis service provided by the analysis service server 31, 32, 33 or the like on the Internet is accessed. When a browser graphic image is displayed on the display unit 11 of the user computer, the URL of the analysis service server 31, 32, 33 or the like is inputted in a URL input field 201, and a read button 202 is clicked, this parameter input graphic image is displayed. While three analysis service servers are herein described as examples, there are in fact many analysis service servers that can be accessed on the Internet. The example herein shows three general analysis service servers among them.

This parameter input graphic image includes a "Sequence Name" input field 203, a "Sequence Type" input field 204, and a "Sequence" input field 205. These input fields are provided with textboxes and/or pull-down menus. Further, the parameter input graphic image includes a "Database" input field 206, a "Matrix" input field 207, a "Threshold" input field 208, a "Priority" select button 209, and an "Analysis" button 210, as options. When the user inputs parameters in necessary input fields, and clicks the "Analysis" button 210, the analysis result display graphic image shown in FIG. 3 is displayed.

FIG. 3 shows an example of a graphic image displaying analysis results by an actual analysis program provided by an analysis service server on the Internet. When the user inputs necessary parameters and clicks the analysis button on the parameter input graphic image of FIG. 2, the analysis program is executed and the analysis result display graphic image of FIG. 3 is displayed.

Analysis results by the bioinformatics analysis program are generally expressed as sets of repletion of a plurality of data structures. For example, FIG. 3 is composed of: a region 301 that begins with a line containing "Sequences producing significant alignments:" and that ends with a line before the line containing "ALIGNMENTS"; a region 302 that begins with a line ">gi|12345678|emb|AL2198129.3| Human DNA sequence from clone" and that ends with a line before the line containing "//", and regions 303 and 304 having the same data structures as that of the region 302. Each of such chunks of data is referred to as a block.

According to the analysis platform of the present invention, analysis results having such block structures are changed to a common format referred to as metadata. Rules for such change are described in the broker program. As described above, the broker program includes the "input parameter information," the "output-data reading information," and the analysis program reference destination." The description thereof will be made in the following.

FIG. 4 shows an example of the input parameter information of which the broker program is composed. The input parameter information is represented as XML documents sandwiched between two tags, "<imputParamInfo> and </imputParamInfo>. The input parameter information can be obtained by analyzing the analysis program input form; that is, input parameters. Each input parameter is defined between two tags, <param> and </param>. In this example, six input parameters 401 to 406 are defined. These input parameters correspond to the input parameters displayed on the parameter input graphic image of FIG. 2.

The definition between <name> and </name> represents each input parameter name displayed on the parameter input graphic image, and the definition between <inputform> and </inputform> represents each input form format, such as a text box, a pull-down menu, or a radio button. The definition between <options> and </options> show a list of alternatives when the input form is a selection type such as a pull-down menu or a list box.

The definition between <defaultVal> and </defaultVal> represents each parameter initial value. The definition between <dataType> and </dataType> represents each data type, such as SEQ or SEQ_TYPE. The definition between <sendName> and </sendName> represents an identifier of each parameter to be sent to the analysis program on the Internet. This corresponds to a NAME attribute of a tag such as <INPUT>, <SELECT>, or <TEXTAREA> of HTML.

For example, in cases in which SEQ is specified as the data type, when characters other than those that can be used for sequence data are inputted, it is possible to return an error when the analysis program is executed. Further, by specifying SEQ or SEQ_TYPE, when an analysis is performed using the analysis platform, it is also possible to automatically input data, such as sequence data, in the input form.

FIG. 5 shows an example of the output-data reading information of which the broker program is composed. The output-data reading information is represented as XML documents sandwiched between two tags, <extractRule> and </extractRule>. Analysis results by the analysis program are generally displayed with block structures, as described above. The output-data reading information associates the definitions of blocks with metadata. Blocks 501 and 502 defined between two tags, <block> and </block>, represent the blocks contained in the analysis results by the analysis program. Two tags, <start> and <end>, are described in an initial portion of each block. These two tags define each block. Namely, they are used for specifying the start and the end of the block. In this example, the first block is specified so that the block begins with the line containing "Sequences producing significant alignments:" and ends with a line before the line containing "ALIGNMENTS." This corresponds to the example of FIG. 3.

The next portion of such block definition is a description for associating the block with a metadata format. For example, when the block is displayed in table format, tags, <table> and </table>, are used, and when the block is displayed in alignment format, <alignment> and </alignment> are used.

In such table or alignment metadata, data necessary for displaying the information thereof is defined in advance. In the present example, the first block 501 is displayed in table format. In this case, necessary data is a table title, a column name, and actual data.

The table title is defined between <TABLE_TITLE> and </TABLE_TITLE>, and each column is described between <COLUMN> and </COLUMN>. The column name of the table is described between <NAME> and </NAME>. Description for specifying the location of cell data in an actual column; that is, the location of data to be retrieved from the block, is made between <DATA> and </DATA>. In this example, the data contents that need to be extracted are specified by using regular expression.

In the present example, the next block 502 is displayed in alignment format. In this case, necessary data includes an alignment score, an E-value, two alignment sequences, the starting locations of the alignment sequences, strands, a sequence name, and lines for representing similarity generally attached between the two alignment sequences. For example, the alignment score is defined between <SCORE> and </SCORE>, and the E-value is defined between <EXPECT> and </EXPECT>. In this way, two tags specify a portion of data that are fetched from the analysis result file, using regular expression.

FIG. 6 shows an example of metadata. Metadata is data obtained by converting analysis results by the analysis program into a format that can be interpreted by the user computer; that is, the analysis platform of the present embodiment. Conversion into metadata is carried out with the output-data reading information 162 of the broker program 160. The analysis platform of the present embodiment displays analysis results based on metadata information. Metadata is represented as XML documents sandwiched between two tags, <metadata> and </metadata>.

The example of metadata shown in FIG. 6 is obtained by converting the analysis results of FIG. 3 using the output-data reading information of FIG. 5. As shown in the figure, the first block 601 of the analysis results is described between <table> and </table>, and each of the three subsequent blocks 602, 603, and 604 of the analysis results is described between <alignment> and </alignment>. These correspond to the blocks 301, 302, 303, and 304 of the analysis results of FIG. 3. Metadata refers to descriptions in XML format of individual blocks of the analysis results, made by using data format defined by the output-data reading information.

Figure 7:
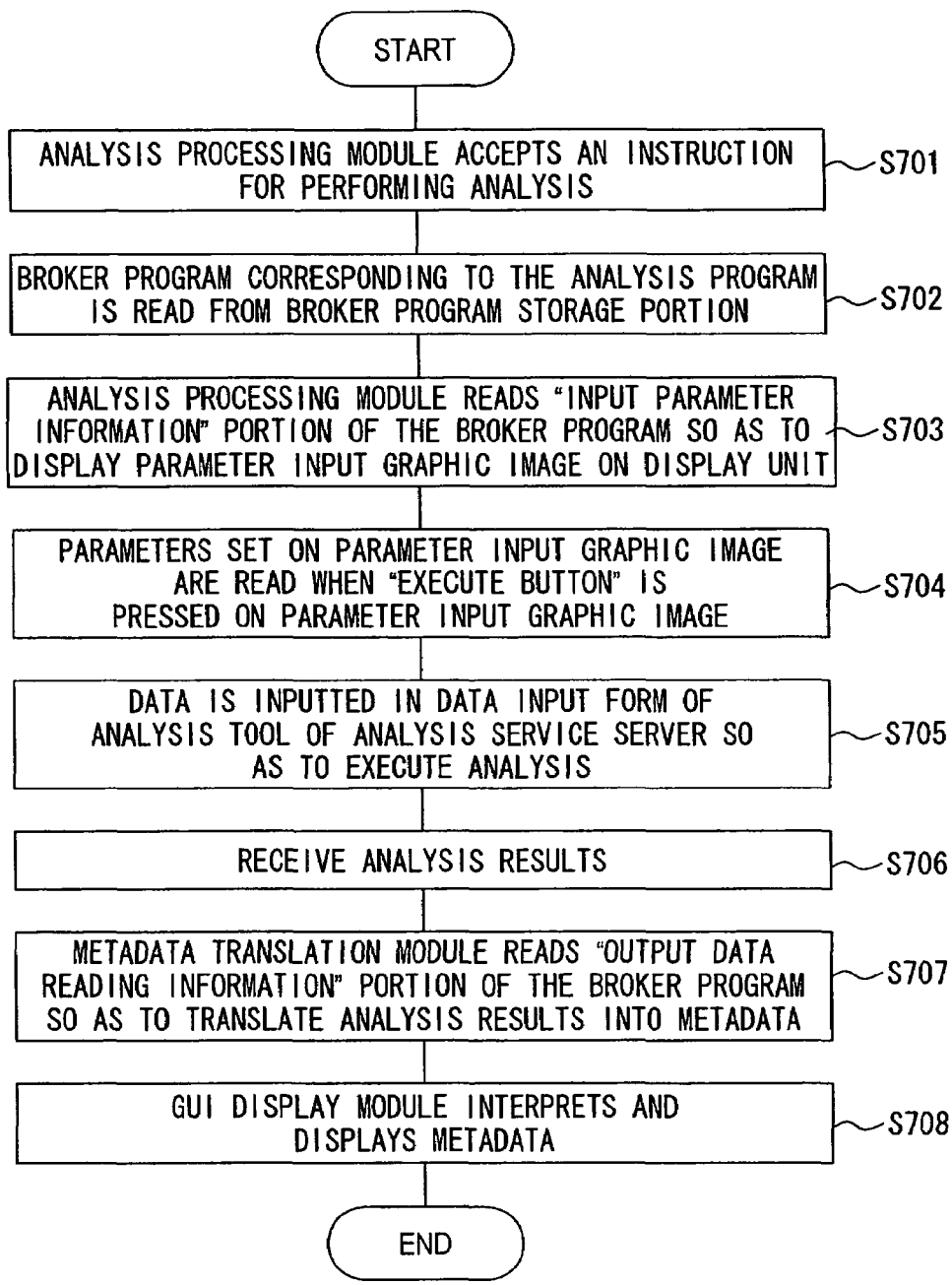
FIG. 7 shows a diagram for explaining a sequence for executing an analysis using the analysis program in an analysis platform (user computer) according to the present invention.

A procedure for executing an analysis with the analysis program by the user computer 1 according to the present invention will be described with reference to FIG. 7. In step S701, the analysis processing module 102 accepts instructions to perform the analysis program from the user. In step S702, the analysis processing module 102 accepts the broker program 160 corresponding to the analysis program from the broker program storage portion 16. In step S703, the analysis processing module 102 reads the input parameter information of the broker program. The GUI display module 101 displays an analysis platform graphic image (FIG. 8) on the display unit 11, using the input parameter information of the broker program 160. In step S704, when the user sets input parameters on the analysis platform graphic image, the analysis processing module 102 reads the parameters. In step S705, the analysis processing module 102 inputs the parameters set by the user in the data input form of the analysis program, so as to execute an analysis. In step S706, the analysis processing module 102 accepts analysis results from the analysis program. In step S707, the metadata translation module 103 reads the output-data reading information of the broker program 160, so as to translate the analysis results into metadata that can be interpreted by the GUI display module. In step S708, the GUI display module 101 interprets and displays the metadata.

FIG. 8 shows an example of an analysis platform graphic image 800 displayed on the display unit of the user computer according to the present invention. The graphic image 800 includes a list 801 of analysis programs, a parameter input form 802, a table viewer 803, and an alignment viewer 804. The parameter input form 802 is created based on the input parameter information of the broker program.

This example shows a case in which the user selects a sequence homology search tool "Analysis Tool A" from the list 801 of analysis programs. When the user sets input parameters of Analysis Tool A in the parameter input form 802 and executes an analysis, analysis results in table format are displayed in the table viewer 803, and analysis results in alignment format are displayed in the alignment viewer 804.

A process for creating the broker program 160 in the analysis platform program 100 will be described with reference to FIG. 9. This process is executed by the broker program creation module 104. The broker program creation module 104 analyzes the input form of the analysis program, so as to obtain input parameter information, and it analyzes the analysis results of test data, so as to obtain output-data reading information.

In step S901, the broker program creation module 104 accepts the URL of the analysis program inputted by the user. The URL of the analysis program is stored in a memory (not shown) of the user computer 1. In step S902, the broker program creation module 104 accesses the URL inputted by the user, so as to obtain the input form of the analysis program. In step S903, the broker program creation module 104 extracts association between the input parameters of the analysis program and the input form displayed on the screen of the display unit of the analysis platform according to the present invention.

In step S904, test data is inputted in the input form of the analysis program. In step S905, analysis processing is executed by the analysis program. In step S906, the analysis results of the test data are displayed on the display unit 11. In step S907, block structures as a result of the analysis are extracted. In step S908, the output-data reading information 162 is generated by associating each block with metadata. In step S909, the input parameter information, the output-data reading information 162, and the above URL of the analysis program stored in the memory are combined together, so as to create the broker program as a file. The process of FIG. 9 will be hereafter described in detail with reference to FIGS. 10 to 20.

Figure 10:
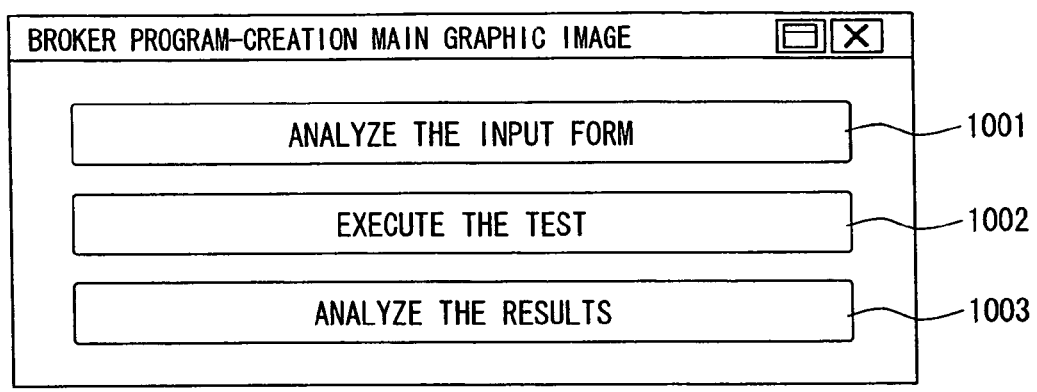
FIG. 10 shows an example of a broker program-creation main graphic image displayed on the display unit of the analysis platform according to the present invention.
Figure 11:
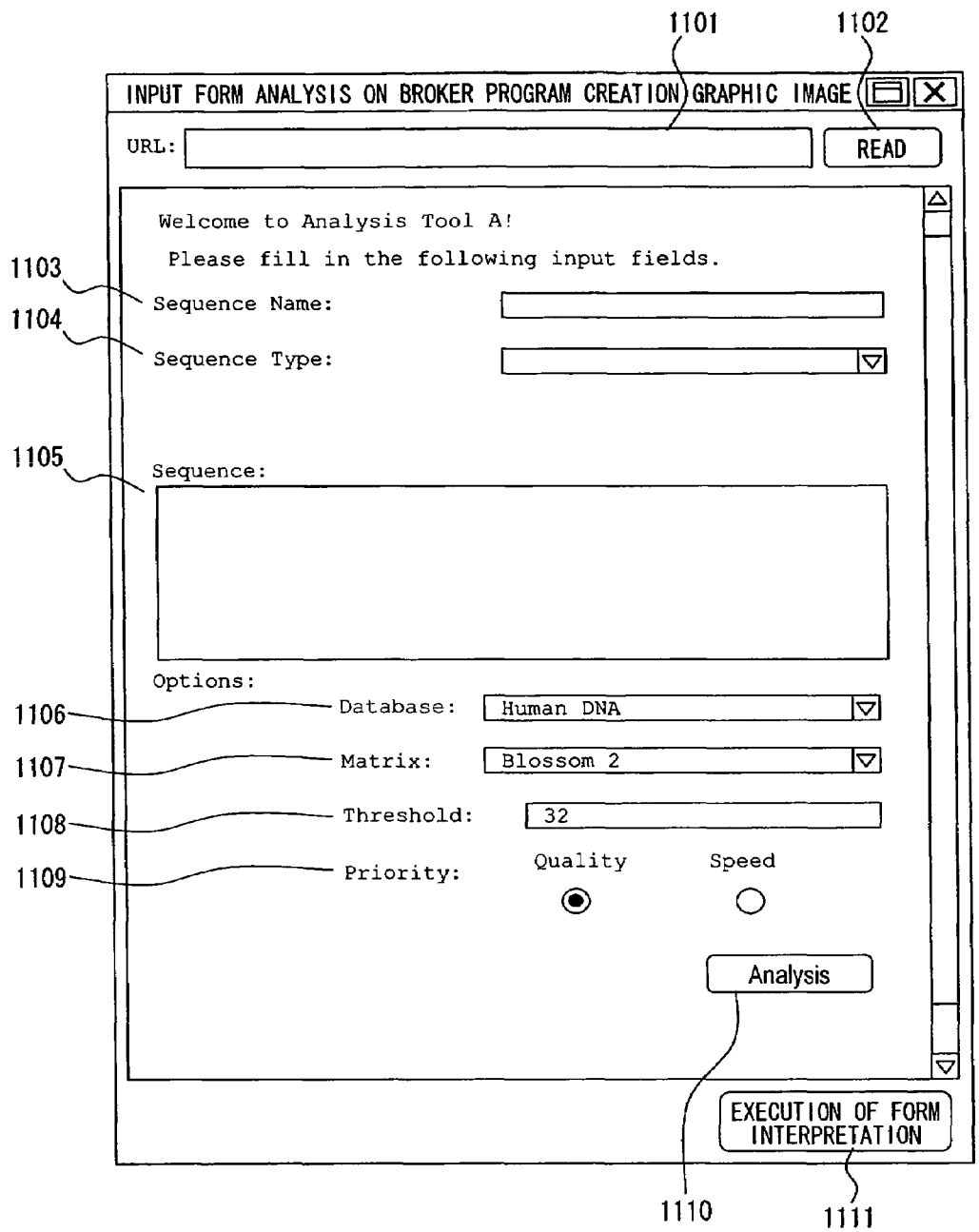
FIG. 11 shows an example of a graphic image for performing a process for analyzing the input form of the analysis program, displayed on the display unit of the analysis platform according to the present invention.
Figure 13:
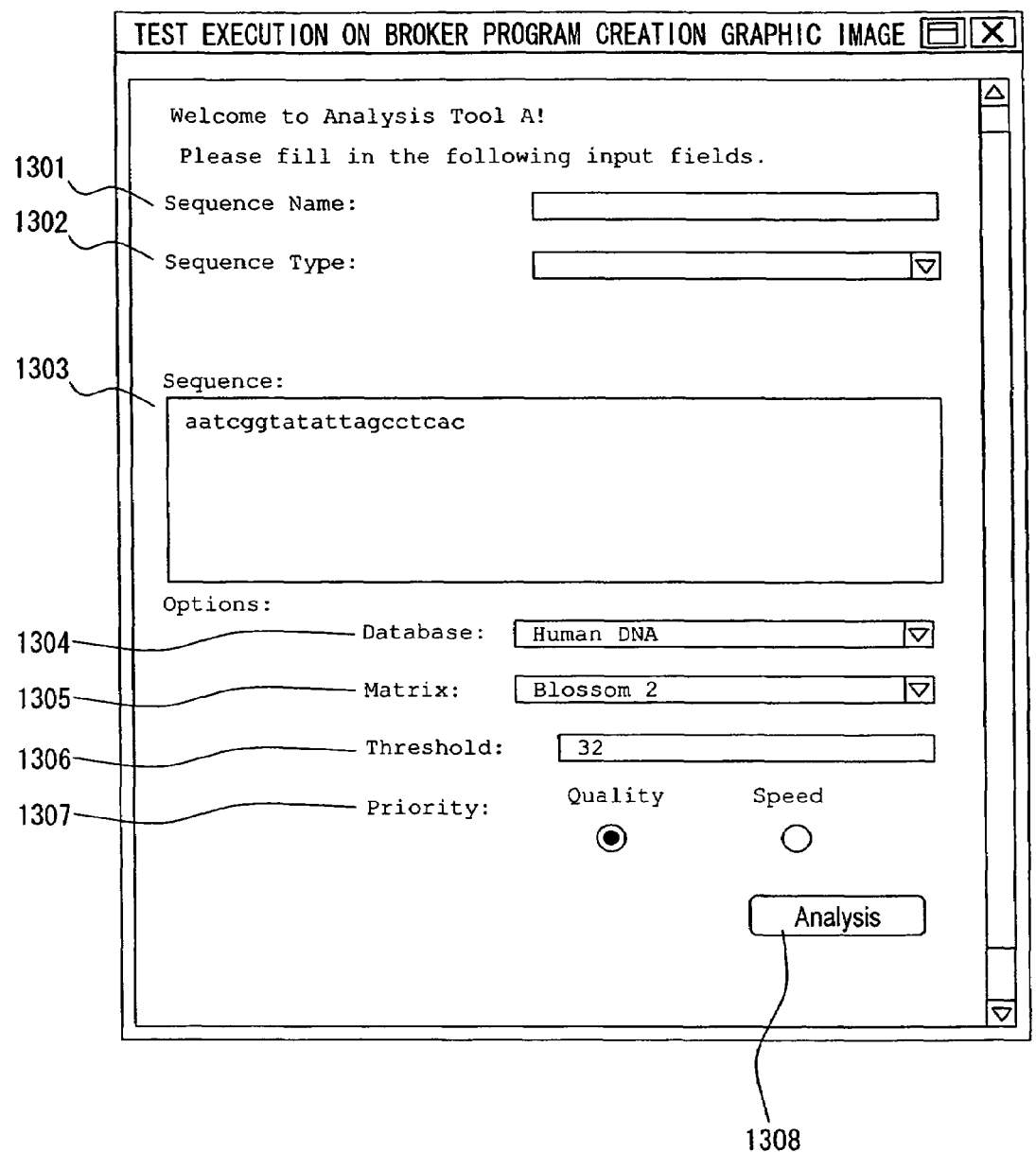
FIG. 13 shows an example of a graphic image for performing a process for inputting test data to the analysis program, displayed on the display unit of the analysis platform according to the present invention.
Figure 15:
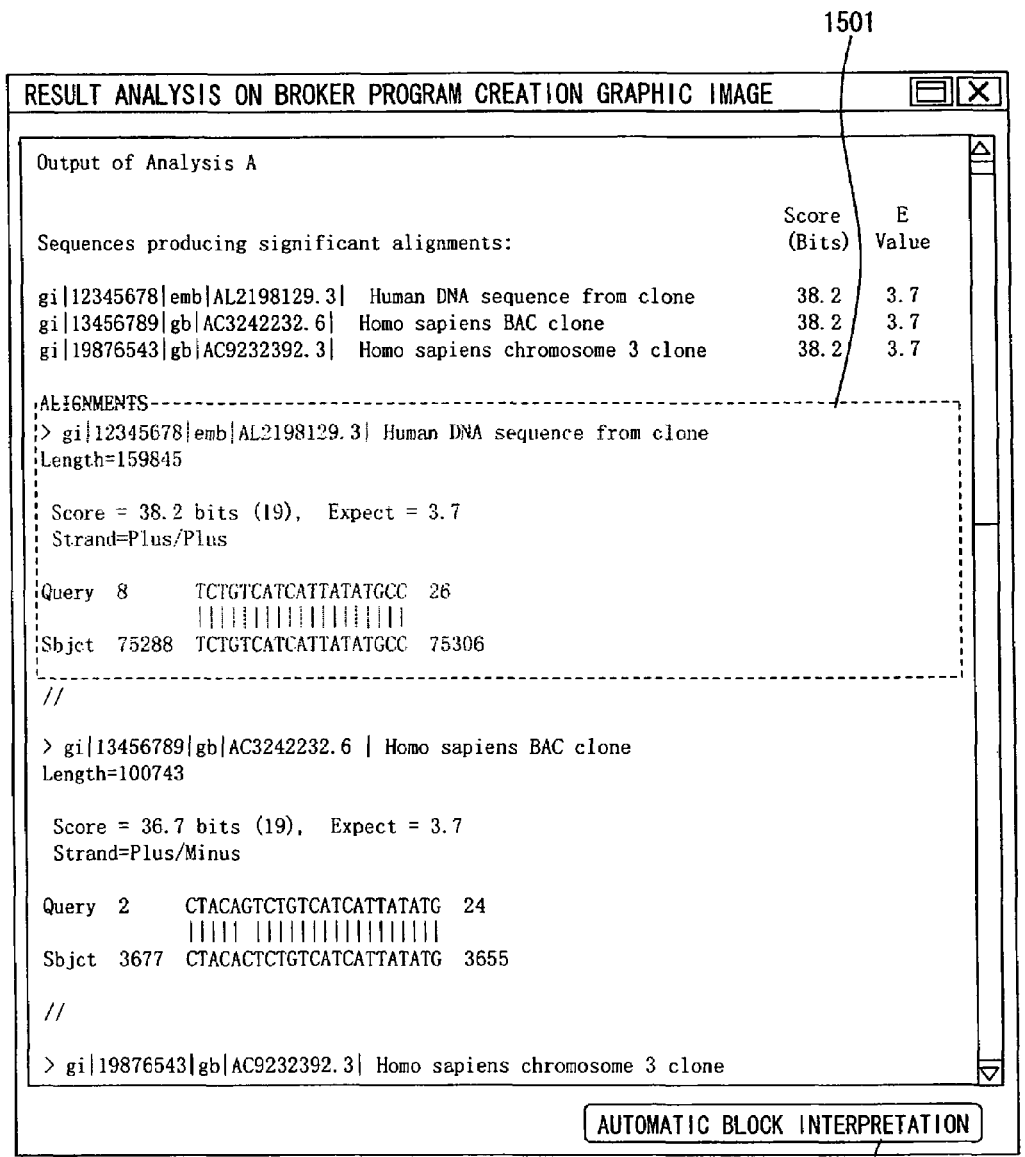
FIG. 15 shows an example of a graphic image for performing a process for extracting blocks from the analysis results, displayed on the display unit of the analysis platform according to the present invention.

FIG. 10 shows an example of the broker program-creation main graphic image. The broker program-creation main graphic image includes an input form analysis button 1001, a test execute button 1002, and a result analysis button 1003. When the input form analysis button 1001 is clicked, the graphic image of FIG. 11 is displayed. Subsequently, the input form of the analysis program is analyzed, and the semantic processing (steps S901 to S903) therefor is executed. When the test execute button 1002 is clicked, the test execution graphic image of FIG. 13 is displayed. Subsequently, test data is inputted to the analysis program, and the processes (steps S904 to S906) for displaying analysis results is executed. When the result analysis button 1003 is clicked, the graphic image of FIG. 15 is displayed. Subsequently, the process for extracting block structures of the analysis results, and the process for associating the block structures with metadata are executed (steps S907 to S909).

Figure 9:
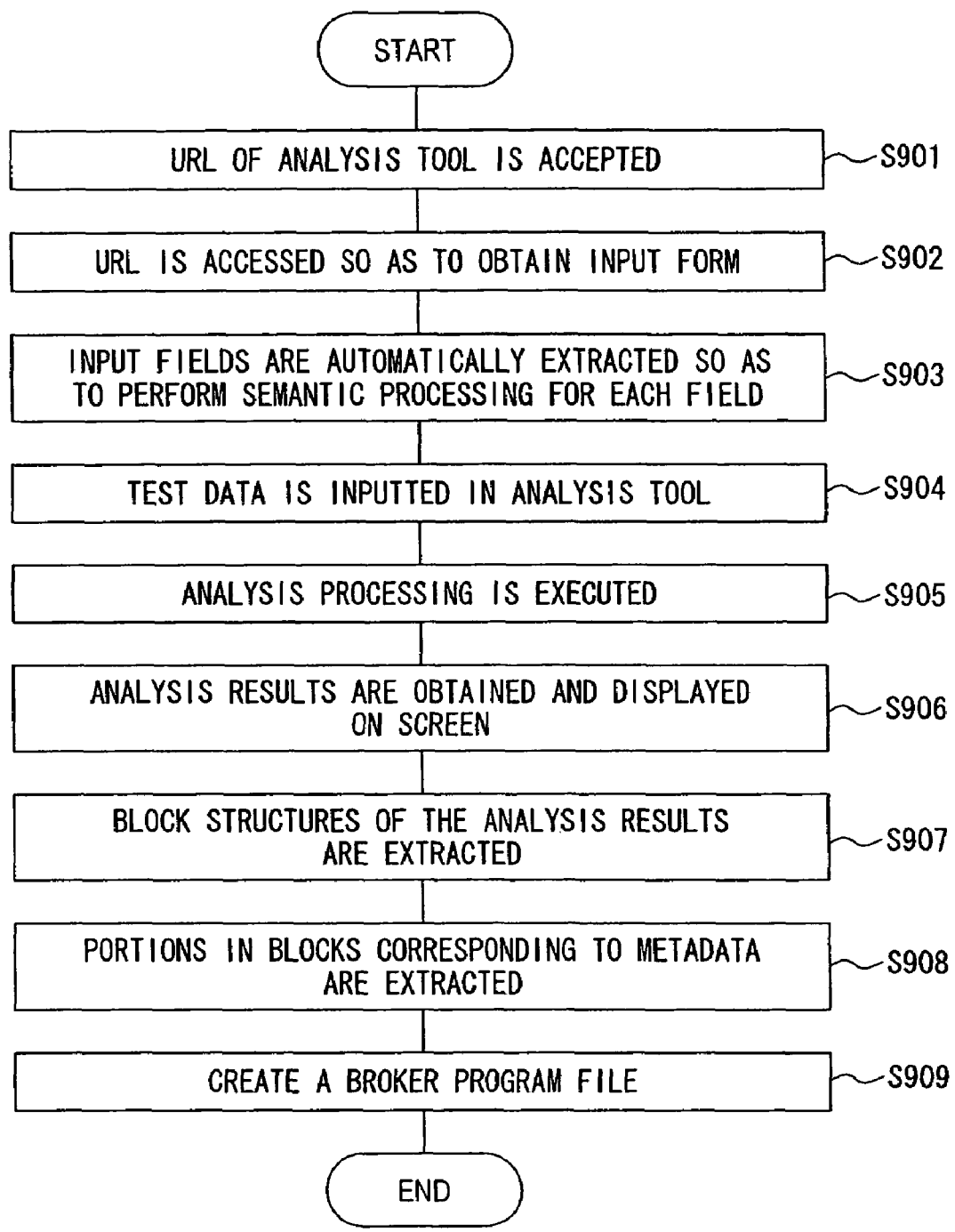
FIG. 9 shows a diagram for explaining a process for creating a broker program in the analysis platform according to the present invention.

FIGS. 11 and 12 show examples of graphic images displayed on the display unit 11 in the processes of steps S901 to S903 of FIG. 9. FIG. 11 shows an example of a graphic image for performing the process for analyzing the input form of the analysis program. The graphic image of FIG. 11 includes a URL input field 1101, a read button 1102, and a form interpretation execute button 1111. When a URL is inputted in the URL input field 1101, and the read button 1102 is clicked, the parameter input graphic image of "Analysis Tool A" as an example of the analysis program is displayed as shown in the figure.

The graphic image of FIG. 11 created by the broker program 160 has the same functions as those of the internet browser and has the same graphic image as that of FIG. 2.

This parameter input graphic image includes a "Sequence Name" input field 1103, a "Sequence Type" input field 1104, and a "Sequence" input field 1105. These input fields are provided with text boxes and/or pull-down menus. Further, it includes a "Database" input field 1106, a "Matrix" input field 1107, a "Threshold" input field 1108, a "Priority" select button 1109, and an "Analysis" button 1110, as options.

While the input fields and buttons 1103 to 1110 are the items (control) of the analysis program, the input field 1101, and buttons 1102 and 1111 are the items (control) on the broker program creation graphic image.

When the form interpretation execute button 1111 is clicked, the input form is interpreted, the input fields are extracted, and the graphic image shown in FIG. 12 is displayed.

FIG. 12 shows an example of a graphic image displaying the results obtained by extracting the input fields from the input form of the analysis program. When the form interpretation execute button 1111 of FIG. 11 is clicked, the graphic image of FIG. 12 is displayed. On this graphic image, input form names 1201, input form types 1202, alternatives 1203, initial values 1204, and data types 1205 are displayed. The input form names 1201 correspond to the input parameters on the parameter input graphic image of FIG. 2. The input form types 1202 include input formats such as a text box, a pull-down menu, and a radio button. The alternatives 1203 indicate all the alternatives contained in each of the input form names 1201. The initial values 1204 are the initial values of the alternatives contained in each of the input form names 1201. The data types 1205 include a sequence, a sequence name, and a sequence type, for example.

The alternatives 1203, the initial values 1204, and the data types 1205 can be edited. For example, when one of the data types 1205 is edited, an alternative is specified using a pull-down menu 1206. When the input parameter information creating button 1207 is clicked, the data is stored in a broker program file as input parameter information of the broker program.

FIGS. 13 and 14 show examples of graphic images displayed on the display unit 11 in the processes of steps S904 to S906 of FIG. 9. FIG. 13 shows an example of a graphic image for performing the process for inputting test data to the analysis program. The graphic image of FIG. 13 is displayed by clicking the test execute button 1002 on the broker program-creation main graphic image of FIG. 10.

The graphic image of FIG. 13 created by the broker program 160 has the same functions as those of the internet browser and has the same graphic image as that of FIG. 2. Thus, this graphic image includes a "Sequence Name" input field 1301, a "Sequence Type" input field 1302, a "Sequence" input field 1303, a "Database" input field 1304, a "Matrix" input field 1305, a "Threshold" input field 1306, a "Priority" select button 1307, and an "Analysis" button 1308. On this graphic image, when the user inputs test data parameters, and clicks the "Analysis" button 1308, the analysis program is executed and the graphic image of FIG. 14 is then displayed.

FIG. 14 shows an example of a graphic image displaying the analysis results obtained through the analysis of the test data by the analysis program. This graphic image is displayed when the analysis execute button 1308 of FIG. 13 is clicked. Based on the analysis results, an operation of extracting block structures and necessary information is carried out, as described below. The graphic image of FIG. 14 shows a state in which results obtained by providing the analysis program read in FIG. 13 with test data and pressing the analysis button of the analysis program itself are displayed.

Figure 16:
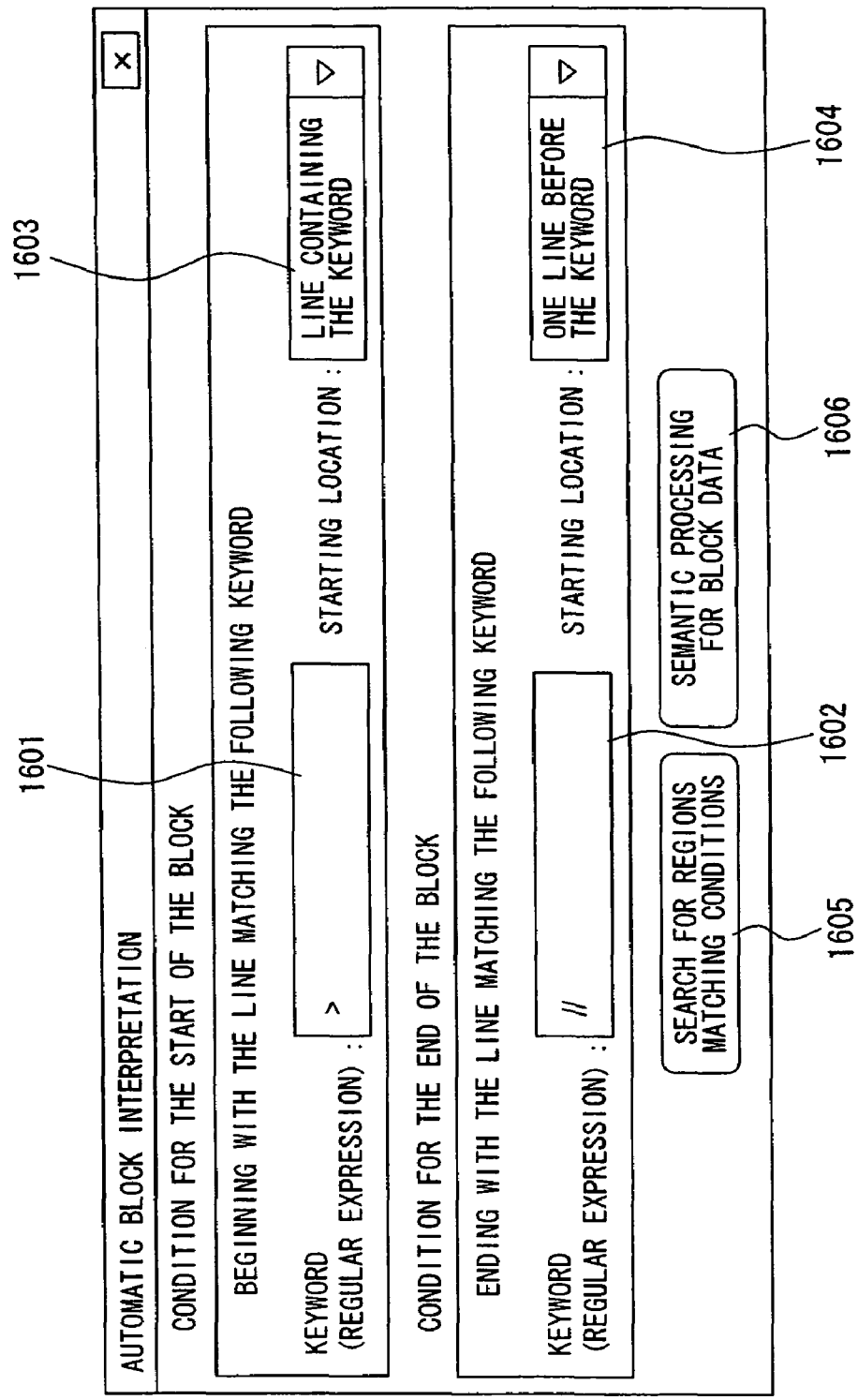
FIG. 16 shows an example of a graphic image for setting conditions for an automatic block interpretation process, displayed on the display unit of the analysis platform according to the present invention.
Figure 17:
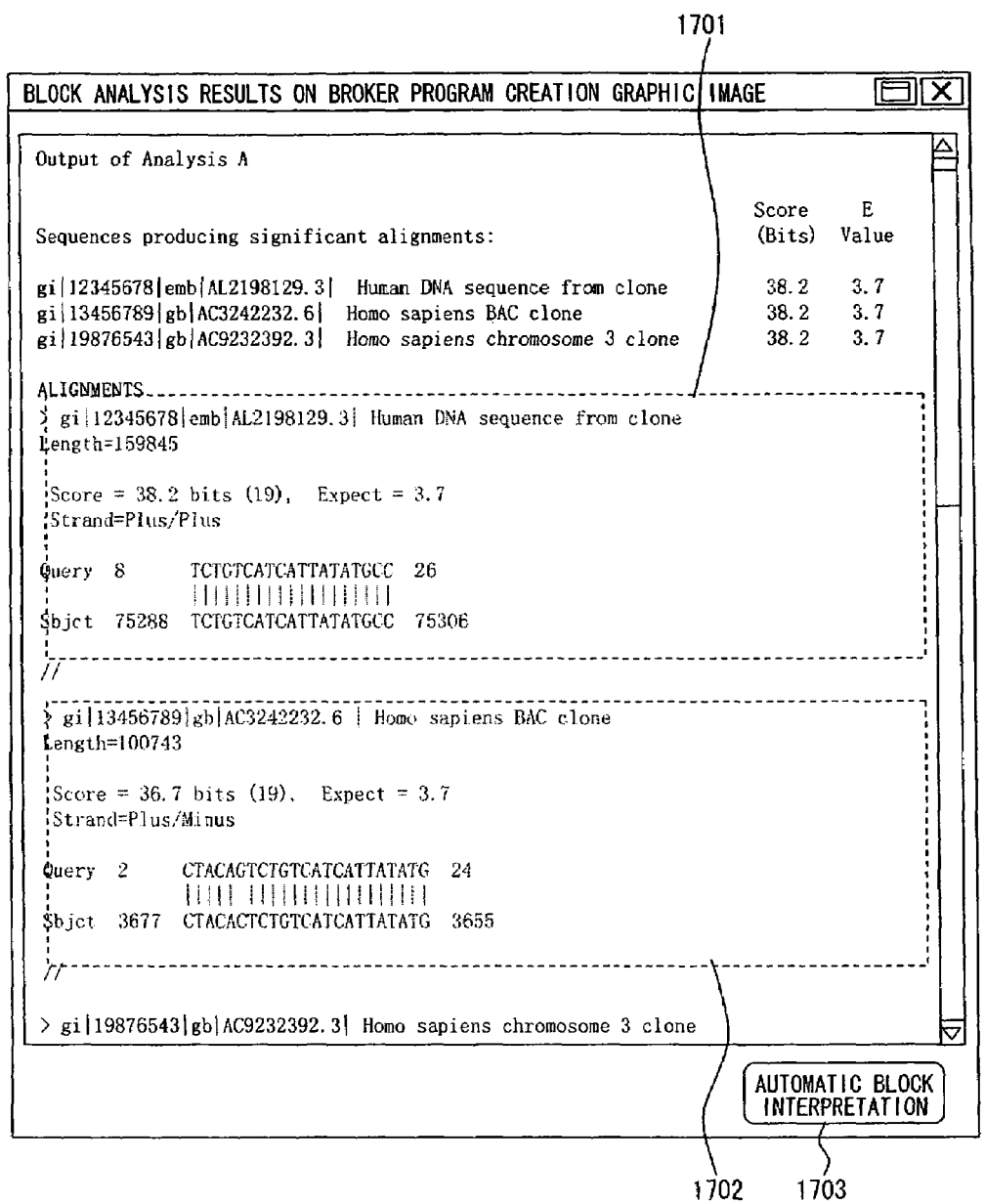
FIG. 17 shows an example of a graphic image displaying the results of the automatic block interpretation process, displayed on the display unit of the analysis platform according to the present invention.

FIGS. 15 to 17 show examples of graphic images displayed on the display unit 11 in the process of step S907 of FIG. 9. FIG. 15 shows an example of a graphic image for performing the process for extracting blocks from the analysis results. The graphic image of FIG. 15 is displayed when the result analysis button 1003 of FIG. 10 is clicked, and it displays the analysis results obtained through the analysis of test data by the analysis program as is the case with the graphic image of FIG. 14. On this graphic image, it can be seen that a block 1501 is formed of lines that begin with a line containing ">" and that end with a line before the line containing "//."

In order to automatically interpret such block, the user specifies the block 1501 with a mouse or the like, and then clicks an automatic block interpretation button 1502. Thus, the conditions of the upper boundary and the lower boundary of the region specified by the user are automatically interpreted. This process is executed by the broker program creation module 104. The details will be hereafter described.

FIG. 16 shows an example of a graphic image for setting conditions for the automatic block interpretation process. The graphic image of FIG. 16 is displayed when the automatic block interpretation button 1502 is clicked on the graphic image of FIG. 15. This graphic image includes a text box 1601 for specifying a keyword relating to a condition for the start of the block, a pull-down menu 1603 for setting the starting location of the block, a text box 1602 for setting a keyword relating to a condition for the end of the block, a pull-down menu 1604 for setting the end location of the block, a button 1605 for searching for regions matching conditions, and a button 1606 for performing a semantic processing for block data.

In the present example, ">" is automatically extracted as a keyword relating to the condition for the start of the block in the text box 1601, and "//" is automatically extracted as a keyword relating to the condition for the end of the block in the text box 1602. Further, the "line containing the keyword ">"" is automatically extracted as the starting location of the block in the pull-down menu 1603, and a "line before the line containing the keyword "//"" is automatically extracted as the end location of the block in the pull-down menu 1604. The pull-down menus 1603 and 1604 include a list including "line containing the keyword," "one line before the keyword," "two lines before the keyword," "one line after . . . ," and the like.

In order to make sure if the conditions are accurately extracted, the user clicks the button 1605 for searching for regions matching conditions. Thus, blocks satisfying the conditions set in the text boxes are searched for. In cases in which blocks are not accurately searched for, the input values in the text boxes 1601 and 1602, and the values in the pull-down menus 1603 and 1604 are corrected, and the button 1605 for searching for regions matching conditions is again clicked. When the button 1605 for searching for regions matching conditions is clicked, the graphic image of FIG. 17 is displayed. Thus, it becomes possible to make sure if accurate blocks have been searched for.

When accurate blocks have been retrieved on the graphic image of FIG. 17, the user returns to the graphic image of FIG. 16 and clicks the button 1606 for performing a semantic processing for block data. In this way, a semantic processing for blocks, which will be described later, is executed, and the graphic image of FIG. 18 is then displayed.

FIG. 17 shows an example of a graphic image displaying the results of the automatic block interpretation process. The graphic image of FIG. 17 is displayed when the button 1605 for searching for regions matching conditions is clicked on the graphic image of FIG. 16. Two blocks 1701 and 1702 are emphatically displayed on this graphic image. The method for emphatic display includes highlighting or the like. In this example, regions satisfying the conditions set on the graphic image of FIG. 16 have been retrieved as blocks.

Figure 18:
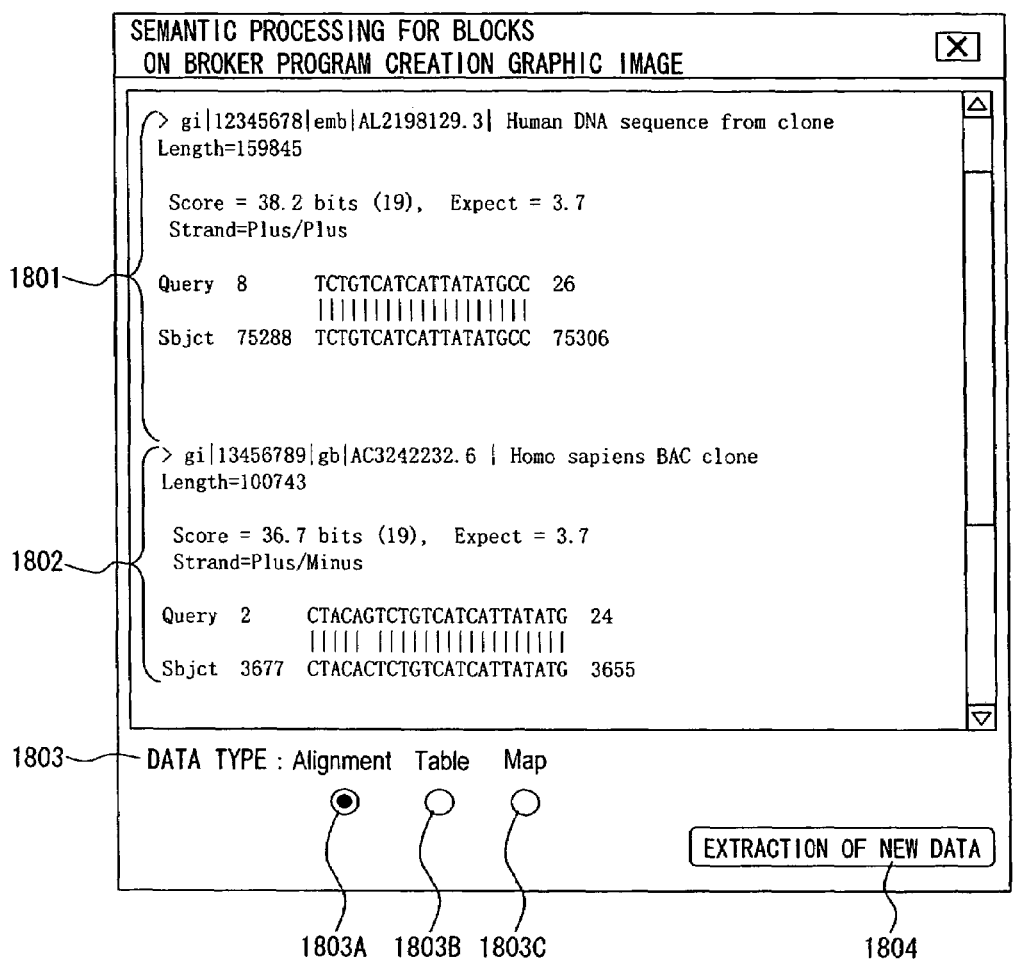
FIG. 18 shows an example of a graphic image for performing a semantic processing for blocks, displayed on the display unit of the analysis platform according to the present invention.
Figure 19:
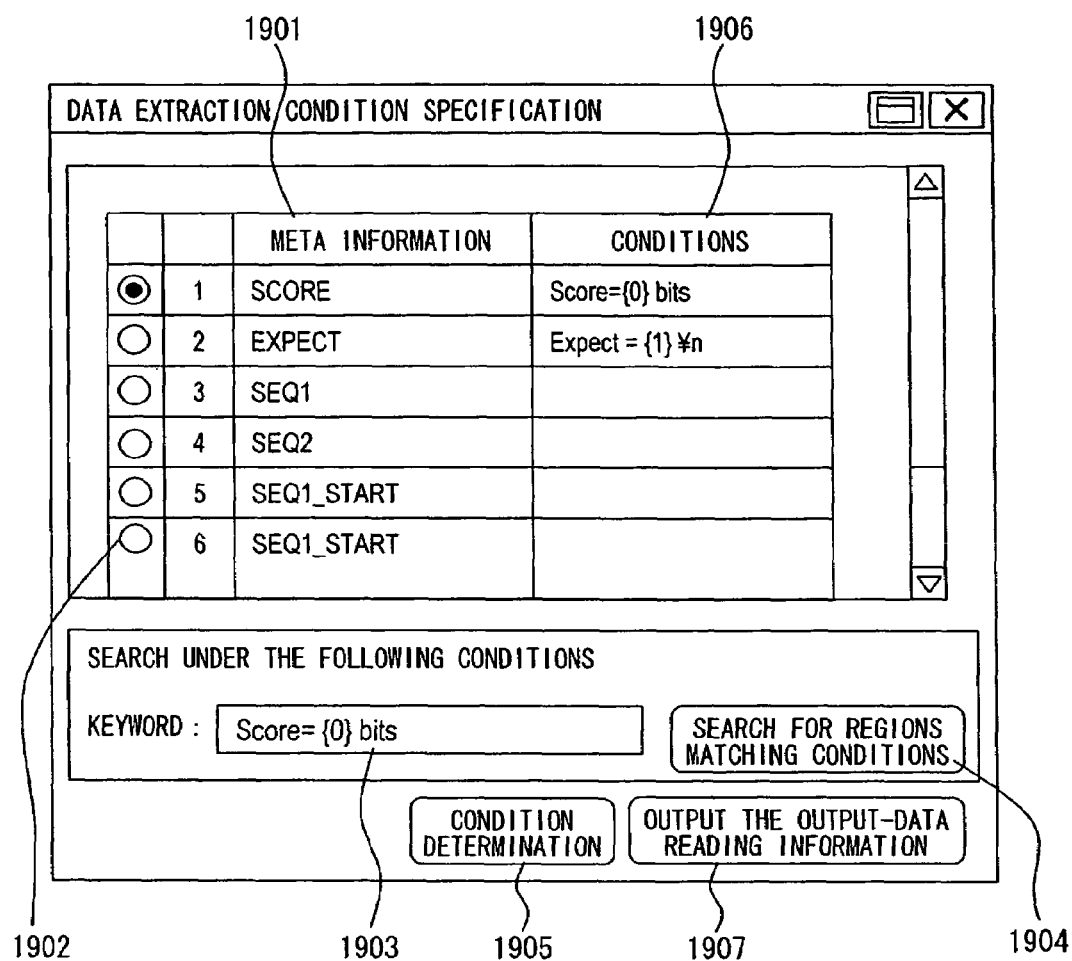
FIG. 19 shows an example of a graphic image for performing the semantic processing for information in the block and meta information, displayed on the display unit of the analysis platform according to the present invention.
Figure 20:
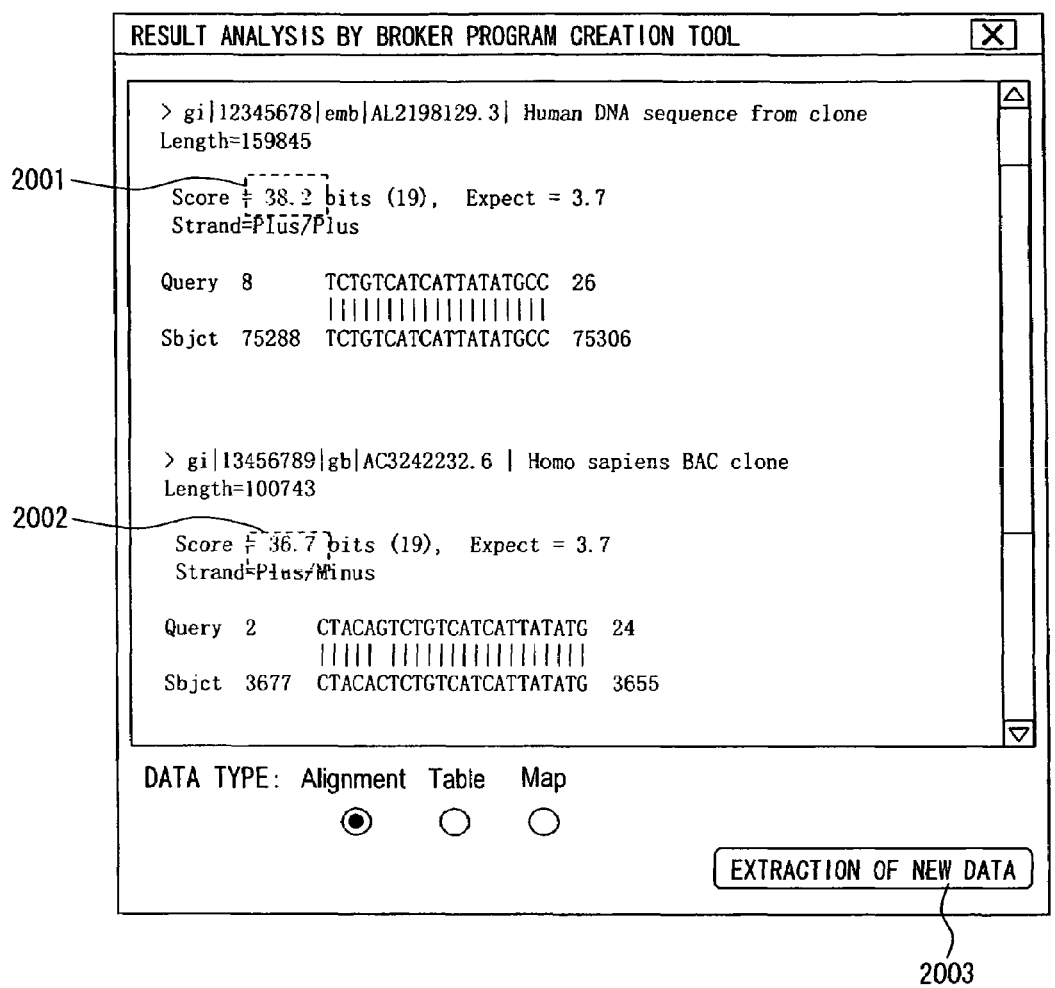
FIG. 20 shows an example of a graphic image displaying the results of the semantic processing for meta information, displayed on the display unit of the analysis platform according to the present invention.

FIGS. 18 to 20 show examples of graphic images displayed on the display unit 11 in the processes of steps S908 and S909 of FIG. 9. FIG. 18 shows an example of a graphic image for performing the semantic processing for blocks. The graphic image of FIG. 18 is displayed when the button 1606 for performing a semantic processing for block data is clicked on the graphic image of FIG. 16. Blocks 1801 and 1802 extracted in the process of step S907 are displayed on this graphic image. This graphic image further includes a field 1803 for selecting a form of data representation and a new data extraction button 1804. The form of representation includes "Alignment" 1803A, "Table" 1803B, and "Map" 1803C, for example. When one of these forms of representation is selected and the new data extraction button 1804 is then clicked, the graphic image of FIG. 19 is displayed. The "Alignment" 1803A has been selected in the example shown in the figure. The description hereafter is made based on the assumption that the "Alignment" 1803A has been selected. While a form of data representation can be selected from the above three forms in this example, the graphic image may be configured such that other forms can be selected.

FIG. 19 shows an example of a graphic image for performing the semantic processing for meta information with respect to information in blocks. The graphic image of FIG. 19 is displayed as a separate window when the new data extraction button 1804 is clicked on the graphic image of FIG. 18. As used herein, the "semantic processing" refers to a process of associating the form of representation on the graphic image of the display unit of the analysis platform with information to be displayed.

The graphic image of FIG. 19 includes meta information 1901 defined in alignments, radio buttons 1902 for selecting meta information, a keyword input field 1903, a button 1904 for searching for regions matching conditions, a condition determination button 1905, condition registration fields 1906, and a button 1907 for outputting output-data reading information. "SCORE," "EXPECT," "SEQ_1," and the like are defined in the alignments as the meta information 1901.

A procedure for performing the semantic processing for meta information will be hereafter described. First, the user selects meta information on which the semantic processing is performed with the radio button 1902. In the example shown in the figure, "SCORE" has been selected. Next, a region in the block on which the semantic processing is performed is specified in the keyword input field 1903. For example, a condition, "Score={0} bits," is specified in the keyword input field 1903.

When the condition is inputted in the keyword input field 1903, the user clicks the button 1904 for searching for regions matching conditions. As a result, regions satisfying the condition set in the keyword input field 1903 are searched for, and thus the graphic image of FIG. 20 is displayed. When a proper condition is not specified, correct regions in blocks cannot be searched for.

In such case, the input value in the keyword input field 1903 is corrected, and the button 1904 for searching for regions matching conditions is again clicked.

FIG. 20 shows an example of a graphic image displaying the results of the semantic processing for meta information. The graphic image of FIG. 20 is displayed when the button 1904 for searching for regions matching conditions is clicked on the graphic image of FIG. 19. Regions 2001 and 2002 in individual blocks are emphatically displayed on this graphic image. The method for emphatic display includes highlighting or the like. These regions 2001 and 2002 correspond to what is retrieved based on the condition "Score={0} bits" set by the user in the keyword input field 1903 on the graphic image of FIG. 19. The process for associating such regions with meta information is performed while the user compares the condition specified on the graphic image of FIG. 19 with the results displayed on the graphic image of FIG. 20.

Upon confirmation of proper block retrieval on the graphic image of FIG. 20, the condition determination button 1905 of FIG. 19 is clicked.

When the condition determination button 1905 is clicked on the graphic image of FIG. 19, the condition inputted in the keyword input field 1903 is displayed in the relevant condition registration field 1906.

On the graphic image of FIG. 19, the semantic processing is performed for the next meta information with respect to blocks. Namely, the next meta information is selected with another radio button 1902, blocks are specified in the keyword input field 1903, and the button 1904 for searching for region matching conditions is then clicked.

Upon completion of the semantic processing for all the meta information listed in the meta information 1901, the user clicks the button 1907 for outputting output-data reading information. The results of the semantic processing for meta information are stored in the broker program 160 as output-data reading information.

Next, by referring to FIGS. 21 and 22, a method by which users share the broker program 160 via the broker program-providing server 2 will be described.

Figure 21:
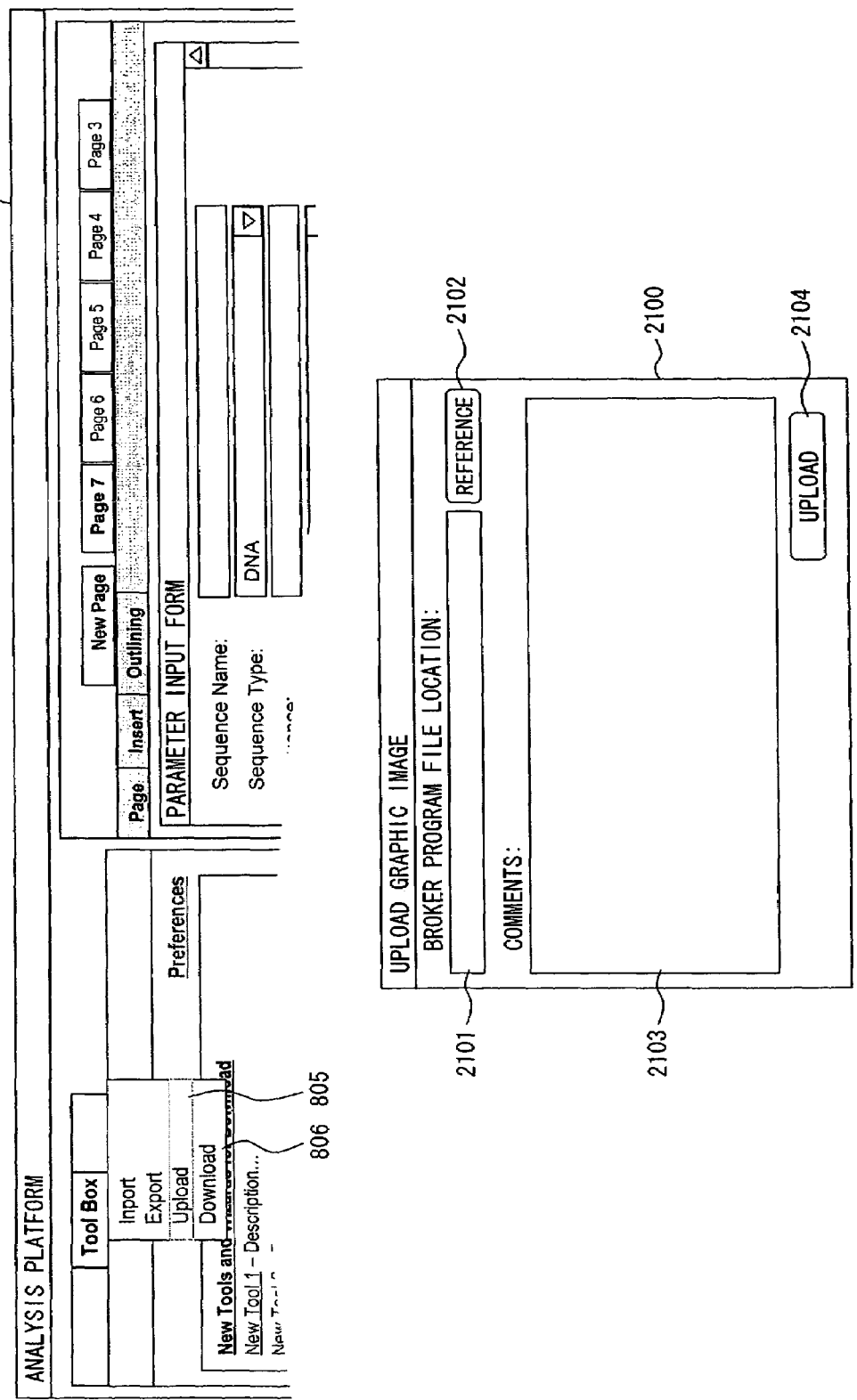
FIG. 21 shows an example of an upload graphic image displayed on the display unit of the analysis platform according to the present invention when the broker program is uploaded to a broker program-providing server.

FIG. 21 shows an example of an upload graphic image displayed on the display unit of the user computer when the broker program is uploaded to the broker program-providing server 2. An upload graphic image 2100 of FIG. 21 is displayed when an upload 805 (see FIG. 21) in the tool box on the analysis platform graphic image 800 shown in FIG. 8 is clicked. The upload graphic image 2100 includes a field 2101 for inputting a broker program file location, a reference button 2102, a comment text box 2103, and an upload button 2104.

The user specifies the broker program file location of the broker program storage portion in the user computer with the reference button 2102. Contents of the broker program file or a message for other users is written in the comment text box 2103. The broker program is sent to the broker program-providing server 2 from the broker program sending/receiving module 105 of the user computer by clicking the upload button 2104. The broker program registration portion 118 of the broker program-providing server 2 stores the broker program in the broker program storage portion 117.

Figure 22:
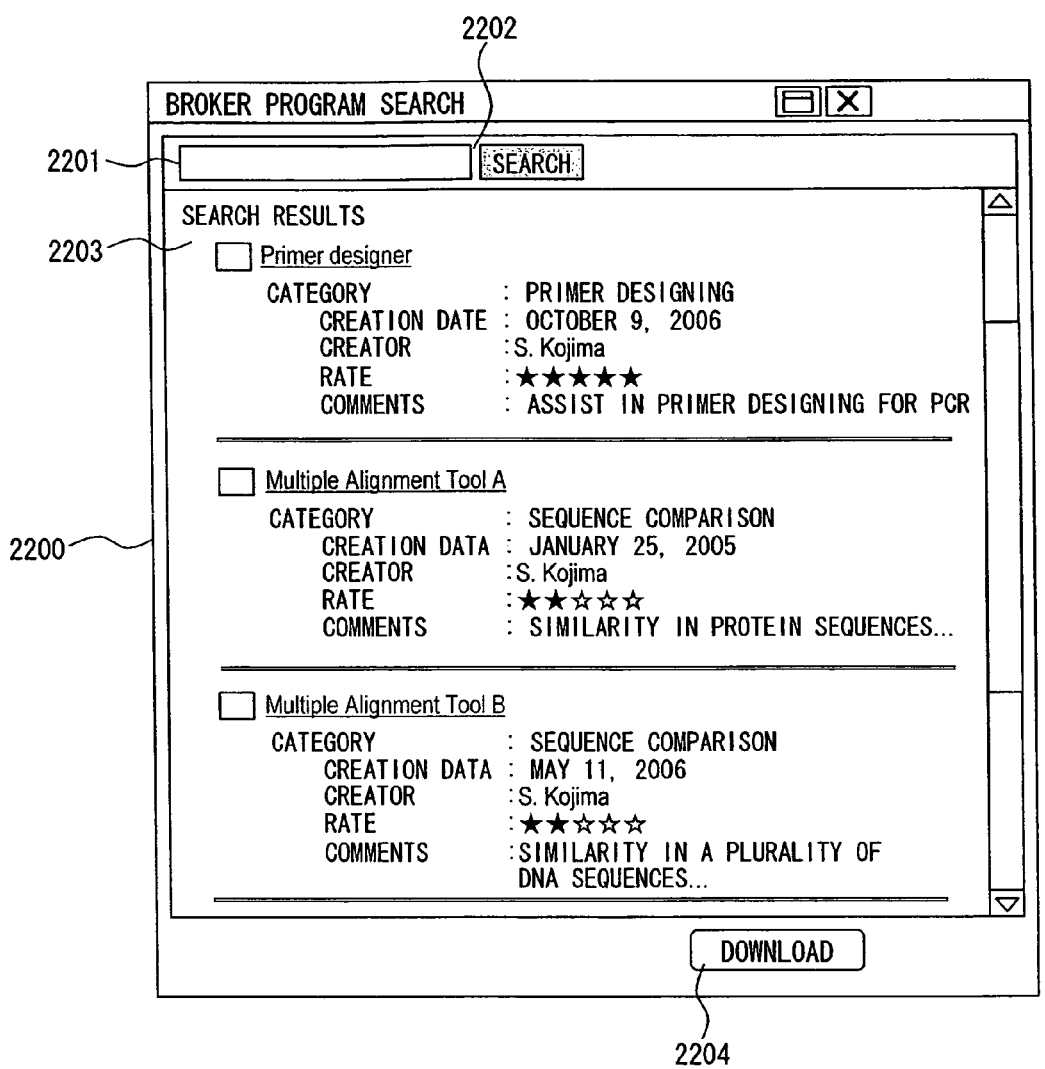
FIG. 22 shows an example of a download graphic image displayed on the display unit of the analysis platform according to the present invention when the broker program is downloaded from the broker program-providing server.

FIG. 22 shows an example of a download graphic image displayed on the display unit of the user computer when the broker program 160 is downloaded from the broker program-providing server 2. A download graphic image 2200 of FIG. 22 is displayed when a download 806 (see FIG. 21) in the tool box on the analysis platform graphic image 800 shown in FIG. 8 is clicked. The download graphic image 2200 includes a keyword input field 2201, a search button 2202, search results 2203, and a download button 2204. When the user inputs a keyword in the field 2201 and clicks the search button 2202, the search results 2203 are displayed. The process for searching for the broker program 160 is executed by the broker program search portion 22.

When a desired broker program 160 is selected from the search results 2203 and the download button 2204 is clicked, the selected broker program 160 is sent to the user computer from the broker program-providing server 2. The broker program 160 is then stored in the broker program storage portion 16 of the user computer.

As shown in the figure, retrieved broker programs 160 are listed in the search results 2203 on the download graphic image 2200. The order in this list may be sorted based on the number of downloads or the level of evaluation by other users, for example. Note that the user computer may be configured such that it notifies the user of up-to-data information by automatically and periodically searching for the broker program 160 that matches the user's field of research registered in advance.

As described above, in the present invention, differences in input/output format between analysis programs are absorbed by the broker program 160. Thus, with the use of such broker program 160, all the analysis programs available on the Internet can be easily downloaded by the user computer.

Further, by registering the broker program 160 in a server that can be accessed by anyone, the broker program 160 can be shared. Thus, since such broker program 160 can be shared by all the researchers, they do not need to conduct a search by covering various analysis programs available on the Internet, and therefore, an analysis program that is up-to-date or suitable for their research can be easily used.

In the system of the present invention, a direct effect of the analysis platform to individual users is that the users can be released from the task of finding an analysis program that has conventionally required many hours, and instead such hours can be spent on their research. Further, even in cases in which a plurality of similar analysis programs exist, by listing individual analysis programs in descending order of evaluation made by other users, the analysis program can be further efficiently selected.

An effect to the field of research in life science as a whole is that since time individual researchers have so far spent can be reduced, the invention can contribute to a further development of research as a whole. This effect increases as the number of users who use the broker programs 160 stored in the server increases.

While examples of the present invention have thus been described, the present invention is not limited to the above examples, and it will be easily understood by a person skilled in the art that various modifications may be made within the scope of the claims.

INDUSTRIAL APPLICABILITY

The present invention can be developed as a software program that obtains the same operational feeling on various operating systems.

SEQUENCE LISTING

```
<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 1
aatcggtata ttagcctcac                                              20

<210> SEQ ID NO 2
<211> LENGTH: 19
<212> TYPE: DNA
<213> ORGANISM: Artificial Sequence
```

```
<220> FEATURE:
<223> OTHER INFORMATION: Description of Artificial Sequence:Synthetic
      DNA

<400> SEQUENCE: 2
tctgtcatca ttatatgcc                                                      19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 3
tctgtcatca ttatatgcc                                                      19

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
ctacagtctg tcatcattat atg                                                 23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5
ctacactctg tcatcattat atg                                                 23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6
tgtcatcatt atatgcctag cat                                                 23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7
tgtcatcatt atatgcttag cat                                                 23

<210> SEQ ID NO 8
<211> LENGTH: 19
<212> TYPE: DNA
<213> ORGANISM: Artificial Sequence
<220> FEATURE:
```

```
<223> OTHER INFORMATION: Description of Artificial Sequence:Synthetic
      DNA

<400> SEQUENCE: 8
tctgtcatca ttatatgcc                                                  19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
tctgtcatca ttatatgcc                                                  19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
aatcggtata ttagcctcac                                                 20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 11
tctgtcatca ttatatgcc                                                  19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 12
tctgtcatca ttatatgcc                                                  19

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 13
ctacagtctg tcatcattat atg                                             23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:Synthetic
```

DNA

<400> SEQUENCE: 14
ctacactctg tcatcattat atg                                    23

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 15
tctgtcatca ttatatgcc                                         19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 16
tctgtcatca ttatatgcc                                         19

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 17
ctacagtctg tcatcattat atg                                    23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 18
ctacactctg tcatcattat atg                                    23

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 19
tctgtcatca ttatatgcc                                         19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

```
<400> SEQUENCE: 20
tctgtcatca ttatatgcc                                                    19

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 21
ctacagtctg tcatcattat atg                                               23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 22
ctacactctg tcatcattat atg                                               23

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 23
tctgtcatca ttatatgcc                                                    19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 24
tctgtcatca ttatatgcc                                                    19

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 25
ctacagtctg tcatcattat atg                                               23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA
```

-continued

```
<400> SEQUENCE: 26
ctacactctg tcatcattat atg                                              23

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 27
tctgtcatca ttatatgcc                                                   19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 28
tctgtcatca ttatatgcc                                                   19

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 29
ctacagtctg tcatcattat atg                                              23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 30
ctacactctg tcatcattat atg                                              23
```

What is claimed is:

1. A method for performing a bioinformatics analysis program on the Internet accessible from a user computer, comprising:

accessing a bioinformatics analysis program;

reading a broker program comprising input parameter information that relates to input parameters extracted from an input form of the analysis program, output-data reading information that represents rules for converting analysis results by the analysis program into metadata to be interpreted by a user computer, and an analysis program reference destination comprising an URL of an analysis program server that provides the analysis program or a file path to the analysis program from the user computer;

creating and displaying an analysis platform graphic image on a screen of a display unit for the user to input parameters based on the input parameter information of the broker program;

executing the analysis program based on the parameters inputted by the user;

converting analysis results by the analysis program into metadata with the output-data reading information of the broker program; and displaying the metadata converted from the analysis results on the screen of the display unit.

2. The method for performing a bioinformatics analysis program according to claim 1, wherein the bioinformatics analysis program is accessed from the user computer.

3. The method for performing a bioinformatics analysis program according to claim 1, wherein the bioinformatics analysis program is stored in the user computer and read therefrom.

4. The method for performing a bioinformatics analysis program according to claim 1, wherein the broker program is stored in the user computer and read therefrom.

5. The method for performing a bioinformatics analysis program according to claim 1, further comprising a step of creating the broker program, wherein the step of creating the broker program comprises:
   extracting input parameters from the input form of the bioinformatics analysis program so as to create the input parameter information;
   creating the output-data reading information based on analysis results obtained by performing the analysis program using test data; and
   synthesizing the input parameter information, the output-data reading information, and the analysis program reference destination.

6. The method for performing a bioinformatics analysis program according to claim 5, further comprising a step of uploading the broker program created in the step of creating the broker program to a broker program-providing server accessible through the Internet.

7. A program embedded in computer-readable for performing a bioinformatics analysis program available on the Internet comprising:
   a module for accessing a bioinformatics analysis program;
   a module for reading a broker program comprising input parameter information that relates to input parameters extracted from an input form of the analysis program, output-data reading information that represents rules for converting analysis results by the analysis program into metadata to be interpreted by a user computer, and an analysis program reference destination comprising an URL of an analysis program server that provides the analysis program or a file path to the analysis program from the user computer;
   a module for creating and displaying an analysis platform graphic image on a screen of a display unit for the user to input parameters based on the input parameter information of the broker program;
   a module for executing the analysis program based on the parameters inputted by the user;
   a module for converting analysis results by the analysis program into metadata with the output-data readable information of the broker program; and
   a module for displaying the metadata converted from the analysis results on the screen of the display unit.

8. A bioinformatics analysis system in which bioinformatics analysis programs available on the Internet are executed by user computers, the system comprising at least one user computer and a broker program-providing server,
   wherein the broker program-providing server makes broker programs available online, each broker program comprising input parameter information that relates to input parameters extracted from an input form of an bioinformatics analysis program, output-data reading information that represents rules for converting analysis results by the analysis program into metadata to be interpreted by the user computer, and an analysis program reference destination, and
   wherein an analysis platform comprises the user computer and downloads from the broker program-providing server a broker program corresponding to the bioinformatics analysis program executed by the user, so as to execute the analysis program with the broker program.

\* \* \* \* \*

UNITED STATES PATENT AND TRADEMARK OFFICE
CERTIFICATE OF CORRECTION

PATENT NO. : 7,647,290 B2  Page 1 of 1
APPLICATION NO. : 11/593173
DATED : January 12, 2010
INVENTOR(S) : Nagai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 531 days.

Signed and Sealed this

Sixteenth Day of November, 2010

David J. Kappos
*Director of the United States Patent and Trademark Office*